United States Patent
Fukumoto et al.

(10) Patent No.: US 11,845,906 B2
(45) Date of Patent: Dec. 19, 2023

(54) FLUORINE-CONTAINING ETHER COMPOUND, LUBRICANT FOR MAGNETIC RECORDING MEDIUM AND MAGNETIC RECORDING MEDIUM

(71) Applicant: Resonac Corporation, Tokyo (JP)

(72) Inventors: Naoya Fukumoto, Ichihara (JP); Daisuke Yagyu, Ichihara (JP); Tsuyoshi Kato, Ichihara (JP); Katsumi Murofushi, Tokyo (JP)

(73) Assignee: RESONAC CORPORATION, Tokyo (JP)

( * ) Notice: Subject to any disclaimer, the term of this patent is extended or adjusted under 35 U.S.C. 154(b) by 39 days.

(21) Appl. No.: 17/765,175

(22) PCT Filed: Sep. 8, 2020

(86) PCT No.: PCT/JP2020/033949
§ 371 (c)(1),
(2) Date: Mar. 30, 2022

(87) PCT Pub. No.: WO2021/065380
PCT Pub. Date: Apr. 8, 2021

(65) Prior Publication Data
US 2022/0380695 A1 Dec. 1, 2022

(30) Foreign Application Priority Data
Oct. 1, 2019 (JP) .................................. 2019-181309

(51) Int. Cl.
*C10M 107/38* (2006.01)
*G11B 5/725* (2006.01)
*C10M 171/04* (2006.01)

(52) U.S. Cl.
CPC ........ *C10M 107/38* (2013.01); *C10M 171/04* (2013.01); *G11B 5/7257* (2020.08); *C10M 2213/0606* (2013.01)

(58) Field of Classification Search
CPC .............. C10M 107/38; C10M 171/04; C10M 2213/0606; G11B 5/7257; C07C 43/225; C08G 65/331
See application file for complete search history.

(56) References Cited

U.S. PATENT DOCUMENTS

2012/0231297 A1  9/2012 Sugiura et al.
2012/0315504 A1* 12/2012 Shimizu ................. C07C 43/23
                                                    428/800

(Continued)

FOREIGN PATENT DOCUMENTS

CN   109937224 A    6/2019
EP   0165650    * 12/1985   ............. C08G 65/00

(Continued)

OTHER PUBLICATIONS

International Search Report for PCT/JP2020/033949 dated Nov. 24, 2020.

(Continued)

*Primary Examiner* — Cephia D Toomer
(74) *Attorney, Agent, or Firm* — Sughrue Mion, PLLC

(57) ABSTRACT

A fluorine-containing ether compound represented by the following formula (1).

$$C_6H_{6-n}\text{—}[O\text{—}R^1\text{—}O\text{—}CH_2\text{—}R^2\text{—}CH_2\text{—}R^3]_n \quad (1)$$

(in the formula (1), n is an integer of 2 or 3, $R^1$ is any one of —$CH_2CH_2$—, —$CH_2CH_2CH_2$— and —$CH_2CH(OH)CH_2$—, $R^2$ is a perfluoropolyether chain, $R^3$ is —$OCH_2CH(OH)CH_2O(CH_2)_m OH$ (m in the formula is an integer of 2 to 4)).

7 Claims, 1 Drawing Sheet

(56) References Cited

U.S. PATENT DOCUMENTS

| | | | |
|---|---|---|---|
| 2013/0209837 A1 | 8/2013 | Sagata et al. | |
| 2014/0368947 A1* | 12/2014 | Saito | C10M 105/54 |
| | | | 427/127 |
| 2015/0371672 A1 | 12/2015 | Sagata | |
| 2016/0203839 A1 | 7/2016 | Shimizu | |
| 2019/0084911 A1 | 3/2019 | Yagyu et al. | |

FOREIGN PATENT DOCUMENTS

| | | |
|---|---|---|
| JP | 4632144 B2 | 2/2011 |
| JP | 2012-184339 A | 9/2012 |
| JP | 2013-18961 A | 1/2013 |
| JP | 5816919 B2 | 11/2015 |
| JP | 6198848 B2 | 9/2017 |
| WO | 2015/093237 A1 | 6/2015 |
| WO | WO-2016084781 A1 * 6/2016 ............. C07C 43/03 |
| WO | 2017/154403 A1 | 9/2017 |
| WO | 2019/039200 A1 | 2/2019 |

OTHER PUBLICATIONS

Zhang Hui-chen et al., "Performances of Lubricants in Hard Disk and Their Influences on Dynamic Characteristics of Magnetic Recording System", Acta Tribology, 2004, vol. 24, No. 5, pp. 476-482 (7 pages).

\* cited by examiner

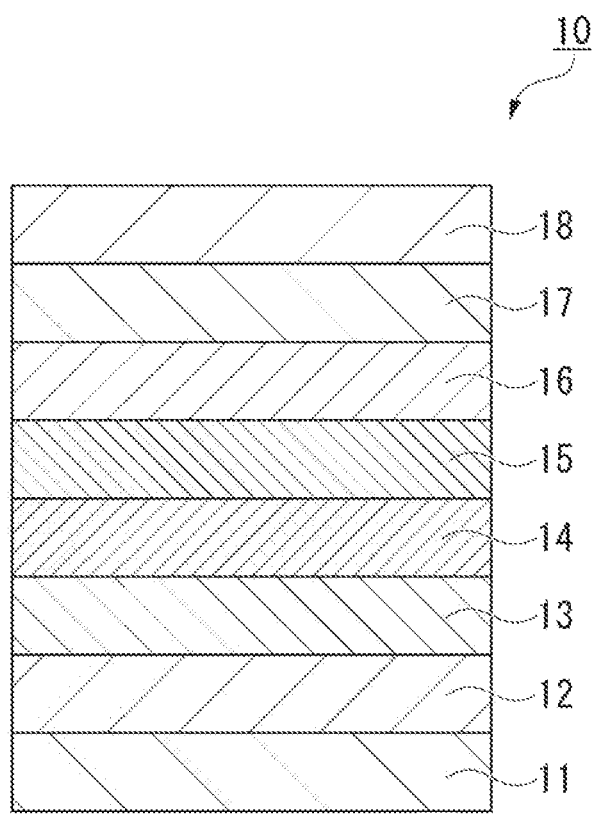

FLUORINE-CONTAINING ETHER COMPOUND, LUBRICANT FOR MAGNETIC RECORDING MEDIUM AND MAGNETIC RECORDING MEDIUM

CROSS REFERENCE TO RELATED APPLICATIONS

This application is a National Stage of International Application No. PCT/JP2020/033949 filed Sep. 8, 2020, claiming priority based on Japanese Patent Application No. 2019-181309 filed Oct. 1, 2019, the contents of which are incorporated herein by reference.

TECHNICAL FIELD

The present invention relates to a fluorine-containing ether compound preferable for application as a lubricant for magnetic recording media, a lubricant for a magnetic recording medium containing the same, and a magnetic recording medium.

BACKGROUND ART

Development of magnetic recording media suitable for high recording densities is underway to improve the recording densities of magnetic recording/reproducing devices.

As a conventional magnetic recording medium, there is a magnetic recording medium in which a recording layer is formed on a substrate and a protective layer made of carbon or the like is formed on the recording layer. The protective layer protects information recorded in the recording layer and enhances the slidability of a magnetic head. However, durability of the magnetic recording medium cannot be sufficiently obtained by simply providing the protective layer on the recording layer. Therefore, it is common to apply a lubricant to the surface of the protective layer to form a lubricating layer.

As the lubricant that is used at the time of forming the lubricating layer in magnetic recording media, for example, lubricants containing a compound having a polar group such as a hydroxyl group at a terminal of a fluorine-based polymer having a repeating structure containing $CF_2$ have been proposed.

For example, Patent Document 1 discloses a fluoropolyether compound having an aromatic group and a hydroxyl group.

In addition, Patent Document 2 discloses a fluoropolyether compound in which a benzene ring is di- or trisubstituted with a fluoropolyether chain having a hydroxyl group at a molecular terminal.

In addition, Patent Document 3 discloses a compound in which a substituent, in which a plurality of hydroxyl groups is present and the shortest distance between the hydroxyl groups is three atoms or more, is disposed at both terminal portions.

CITATION LIST

Patent Document

[Patent Document 1]
Japanese Patent No. 5816919
[Patent Document 2]
Japanese Patent No. 6198848
[Patent Document 3]
Japanese Patent No. 4632144

SUMMARY OF INVENTION

Technical Problem

There is a demand for a further decrease in the flying height of a magnetic head in magnetic recording/reproducing devices. This requires a further decrease in the thickness of lubricating layers in magnetic recording media.

However, usually, there is a tendency that a decrease in the thicknesses of lubricating layers degrades the coatability of the lubricating layers and thereby degrades the wear resistance of magnetic recording media. In addition, when the thickness of the lubricating layer is decreased, the adhesion between the lubricating layer that coats the surface of a protective layer and the protective layer becomes insufficient, and pickup, which is the attachment of a fluorine-containing ether compound in the lubricating layer to a magnetic head, is likely to occur.

The present invention has been made in consideration of the above-described circumstances, and an objective of the present invention is to provide a fluorine-containing ether compound that enables the formation of a lubricating layer in which wear resistance is excellent and pickup is suppressed in spite of a thin thickness and can be preferably used as a material for lubricants for magnetic recording media.

In addition, another objective of the present invention is to provide a lubricant for a magnetic recording medium containing the fluorine-containing ether compound of the present invention.

In addition, still another objective of the present invention is to provide a magnetic recording medium having a lubricating layer containing the fluorine-containing ether compound of the present invention and having excellent reliability and durability.

Solution to Problem

The present inventors repeated intensive studies to solve the above-described problem.

As a result, the present inventors found that a fluorine-containing ether compound in which two or three hydrogen atoms in a benzene ring are substituted with substituents, in which a perfluoropolyether chain to which a terminal group composed of $-OCH_2CH(OH)CH_2O(CH_2)_mOH$ (m in the formula is an integer of 2 to 4) is bonded through a methylene group ($-CH_2-$) is bonded to a specific linking group, is capable of solving the above-described problem and conceived the present invention.

That is, a first aspect of the present invention is the following fluorine-containing ether compound.

[1] A fluorine-containing ether compound represented by the following formula (1).

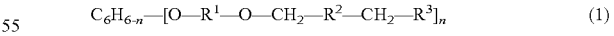

$$C_6H_{6-n}-[O-R^1-O-CH_2-R^2-CH_2-R^3]_n \qquad (1)$$

(in the formula (1), n is an integer of 2 or 3, $R^1$ is any one of $-CH_2CH_2-$, $-CH_2CH_2CH_2-$ and $-CH_2CH(OH)CH_2-$, $R^2$ is a perfluoropolyether chain, and $R^3$ is $-OCH_2CH(OH)CH_2O(CH_2)_mOH$ (m in the formula is an integer of 2 to 4)).

The fluorine-containing ether compound of the first aspect of the present invention may preferably have the following characteristics as described below. Two or more of the following characteristics may be preferably combined.

[2] The fluorine-containing ether compound according to [1], in which $R^2$ in the formula (1) is represented by any one of the following formulae (2) to (4).

(2)
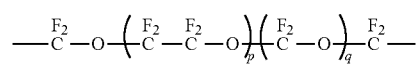
(3)
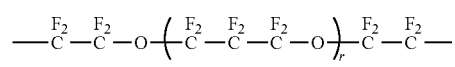
(4)
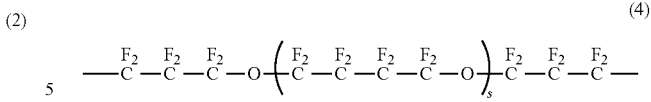
(In the formula (2), p represents 1 to 30, and q represents 0 to 30.)
(In the formula (3), r represents 1 to 30.)
(In the formula (4), s represents 1 to 20.)
[3] The fluorine-containing ether compound according to [2], wherein the compound is any one of compounds represented by the following formulae (A) to (N).
(A)
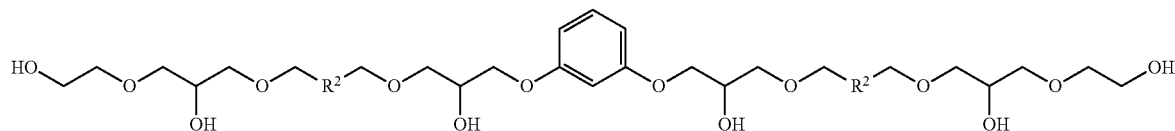
(B)
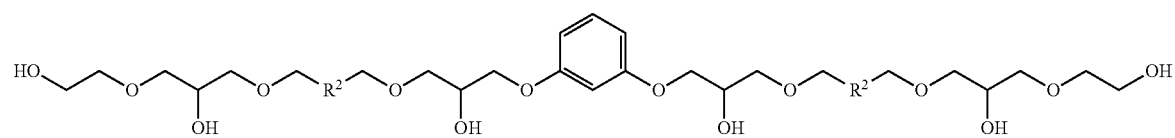
(C)
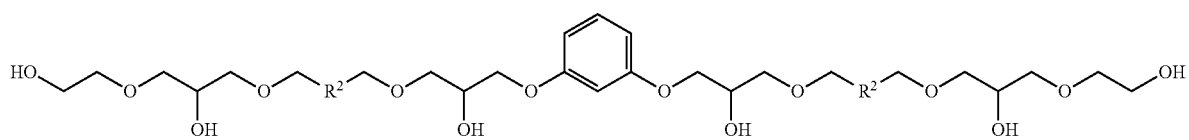
(D)
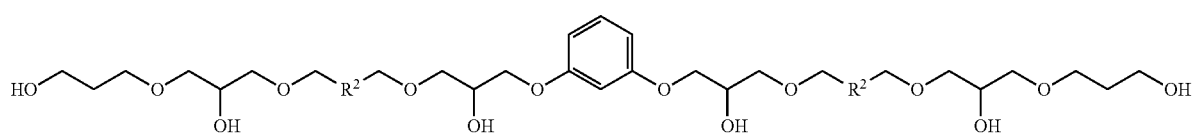
(E)
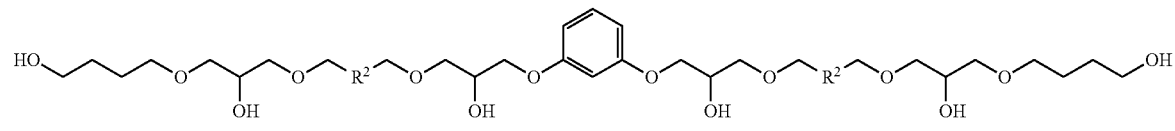
(F)
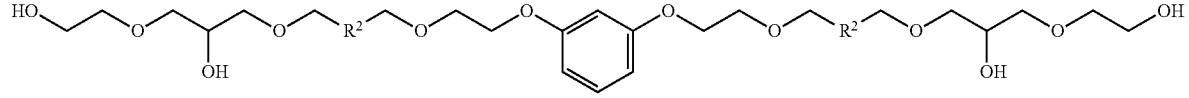
(G)
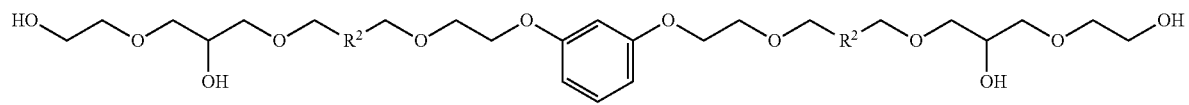
(H)
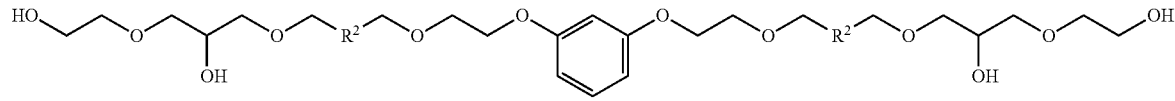

(In the formula (A), $R^2$ is represented by the formula (2).)
(In the formula (B), $R^2$ is represented by the formula (3).)
(In the formula (C), $R^2$ is represented by the formula (4).)
(In the formula (D), $R^2$ is represented by the formula (2).)
(In the formula (E), $R^2$ is represented by the formula (2).)
(In the formula (F), $R^2$ is represented by the formula (2).)
(In the formula (G), $R^2$ is represented by the formula (3).)
(In the formula (H), $R^2$ is represented by the formula (4).)

(In the formula (I), $R^2$ is represented by the formula (2).)
(In the formula (J), $R^2$ is represented by the formula (2).)
(In the formula (K), $R^2$ is represented by the formula (3).)
(In the formula (L), $R^2$ is represented by the formula (4).)
(In the formula (M), $R^2$ is represented by the formula (2).)
(In the formula (N), $R^2$ is represented by the formula (2).)

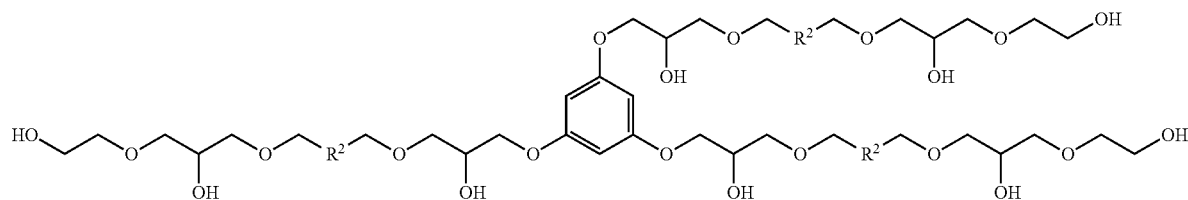

(I)

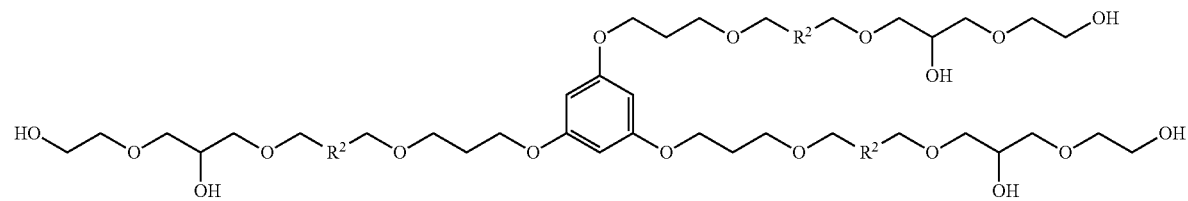

(J)

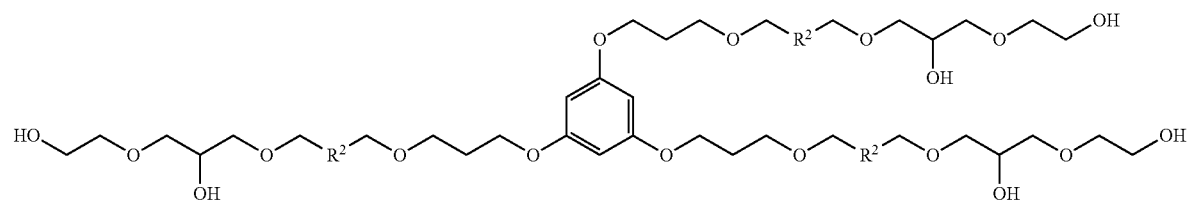

(K)

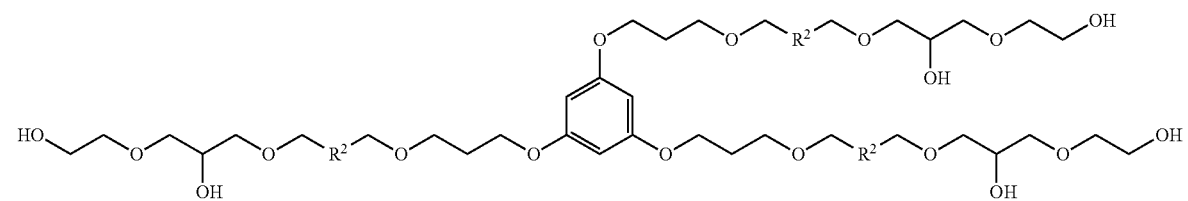

(L)

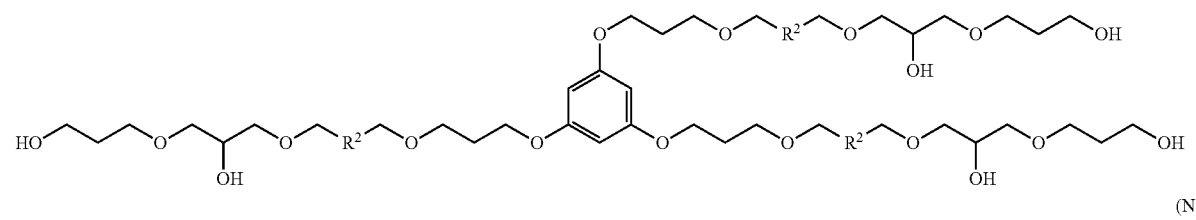

(M)

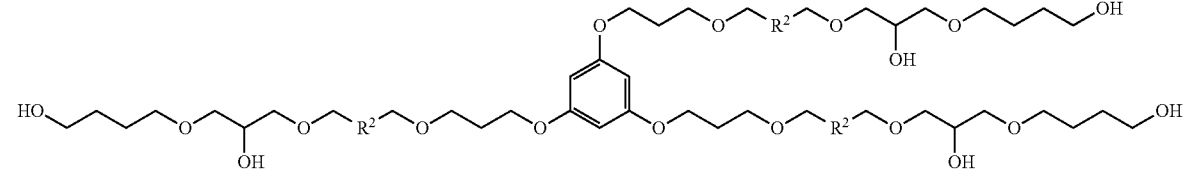

(N)

[4] The fluorine-containing ether compound according to any one of [1] to [3], in which a number-average molecular weight thereof is within a range of 500 to 10000.

[5] A lubricant for a magnetic recording medium containing the fluorine-containing ether compound according to any one of [1] to [4].

[6] A magnetic recording medium including at least a magnetic layer, a protective layer and a lubricating layer sequentially provided on a substrate, in which the lubricating layer contains the fluorine-containing ether compound according to any one of [1] to [4].

[7] The magnetic recording medium according to [6], in which the lubricating layer has an average film thickness of 0.5 nm to 3 nm.

Advantageous Effects of Invention

The fluorine-containing ether compound of the present invention is preferable as a material for lubricants for magnetic recording media.

The lubricant for a magnetic recording medium of the present invention contains the fluorine-containing ether compound of the present invention and thus enables the formation of a lubricating layer in which wear resistance is excellent and pickup is suppressed in spite of a thin thickness.

The magnetic recording medium of the present invention is provided with a lubricating layer in which wear resistance is excellent and pickup is suppressed and thus has excellent reliability and durability.

BRIEF DESCRIPTION OF DRAWINGS

FIG. 1 is a schematic cross-sectional view showing an embodiment of a magnetic recording medium of the present invention.

DESCRIPTION OF EMBODIMENTS

Hereinafter, preferable examples of a fluorine-containing ether compound, a lubricant for a magnetic recording medium (hereinafter, abbreviated as "lubricant" in some cases) and a magnetic recording medium of the present invention will be described in detail. The present invention is not limited only to an embodiment described below. Within the scope of the present invention, numbers, positions, types, amounts, ratios, combinations, numerical values, sizes, and the like can be omitted, changed and/or added as necessary.

[Fluorine-Containing Ether Compound]

A fluorine-containing ether compound of the present embodiment is represented by the following formula (1).

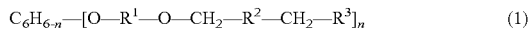
$$C_6H_{6-n}\text{—}[O\text{—}R^1\text{—}O\text{—}CH_2\text{—}R^2\text{—}CH_2\text{—}R^3]_n \quad (1)$$

(in the formula (1), n is an integer of 2 or 3, $R^1$ is any one of —$CH_2CH_2$—, —$CH_2CH_2CH_2$— and —$CH_2CH(OH)CH_2$—, $R^2$ is a perfluoropolyether chain, $R^3$ is —$OCH_2CH(OH)CH_2O(CH_2)_m OH$ (m in the formula is an integer of 2 to 4)).

Here, the reason that excellent wear resistance can be obtained and pickup is suppressed in spite of a thin thickness in a case where a lubricating layer is formed on a protective layer of a magnetic recording medium using a lubricant containing the fluorine-containing ether compound of the present embodiment will be described.

The fluorine-containing ether compound of the present embodiment has a structure in which, as shown in the formula (1), two or three hydrogen atoms in the benzene ring are substituted with substituents (—[O—$R^1$—O—$CH_2$—$R^2$—$CH_2$—$R^3$]).

The benzene ring that is contained in the fluorine-containing ether compound represented by the formula (1) contributes to improvement in the adhesion between the fluorine-containing ether compound of the present embodiment and a protective layer by the intermolecular interaction of the benzene ring and/or the interaction between the benzene ring and the protective layer. Therefore, the use of a lubricant containing the fluorine-containing ether compound represented by the formula (1) makes it possible to obtain lubricating layers having excellent wear resistance.

The two or three substituents that are contained in the fluorine-containing ether compound represented by the formula (1) each have one perfluoropolyether chain represented by $R^2$ (hereinafter, abbreviated as "PFPE chain" in some cases). The PFPE chain coats the surface of a protective layer and also imparts lubricity to a lubricating layer to reduce the friction force between a magnetic head and the protective layer in the case of forming the lubricating layer by applying a lubricant containing the fluorine-containing ether compound onto the protective layer.

As shown in the formula (1), a terminal group represented by $R^3$ bonds to an end portion of the PFPE chain represented by $R^2$ opposite to the benzene ring through a methylene group (—$CH_2$—). The terminal group represented by $R^3$ is composed of —$OCH_2CH(OH)CH_2O(CH_2)_m OH$ (m in the formula is an integer of 2 to 4). Two hydroxyl groups (—OH) that are included in the terminal group represented by $R^3$ attach the fluorine-containing ether compound and the protective layer and thereby suppress pickup in the lubricating layer containing the fluorine-containing ether compound of the present embodiment.

In the terminal group represented by $R^3$, the two hydroxyl groups (—OH) bond to different carbon atoms, and the carbon atoms to which the hydroxyl groups bond bond to each other through a linking group including an oxygen atom (a linking group including —O— (ether bond)). The linking group including an ether bond imparts flexibility to the terminal group represented by $R^3$. Therefore, compared with, for example, a fluorine-containing ether compound in which two hydroxyl groups that are included in a terminal group bond to different carbon atoms, and the carbon atoms to which the hydroxyl groups bond bond to each other, a lubricating layer containing the fluorine-containing ether compound of the present embodiment is easily adsorbed to a protective film and is excellent in terms of adhesion between the lubricating layer and the protective layer.

In addition, in the fluorine-containing ether compound represented by the formula (1), the linking group (—O—$R^1$—O—$CH_2$—) including an ether bond (—O—) is disposed between the benzene ring and the PFPE chain represented by $R^2$. The linking group including an ether bond imparts flexibility to the fluorine-containing ether compound represented by the formula (1). Therefore, compared with, for example, a fluorine-containing ether compound in which a benzene ring and the PFPE chain represented by $R^2$ directly bond to each other, a lubricating layer containing the fluorine-containing ether compound of the present embodiment is easily adsorbed to a protective film and is excellent in terms of the adhesion between the lubricating layer and the protective layer.

From this fact, it is assumed that a lubricant containing the fluorine-containing ether compound of the present embodiment is capable of coating the surface of a protective layer at a high coating rate in spite of a thin thickness and enables the formation of a lubricating layer in which wear resistance is excellent and pickup is suppressed.

In the fluorine-containing ether compound represented by the formula (1), the number of substituents (—[O—$R^1$—O—$CH_2$—$R^2$—$CH_2$—$R^3$]) bonding to the benzene ring (the number of n in the formula (1)) is two or three.

The two or three substituents bonding to the benzene ring may be different from each other or may include substituents that are the same as each other. The two or three substituents are preferably all the same since the synthesis of the fluorine-containing ether compound is easy.

In a case where the two or three substituents that are included in the fluorine-containing ether compound represented by the formula (1) include substituents that are not the same as each other, $R^1$, $R^2$ and $R^3$ that are included in each substituent may be all different from each other or only one or two of $R^1$, $R^2$ and $R^3$ may be different from the others.

In the fluorine-containing ether compound of the present embodiment represented by the formula (1), $R^1$ is any one of —$CH_2CH_2$—, —$CH_2CH_2CH_2$— and —$CH_2CH(OH)CH_2$—.

In a case where $R^1$ is —$CH_2CH(OH)CH_2$—, the hydroxyl group (—OH) that is included in $R^1$ attaches the fluorine-containing ether compound and a protective layer and thereby suppresses pickup in a lubricating layer containing the fluorine-containing ether compound of the present embodiment, which is preferable.

Particularly, in a case where the number of n in the formula (1) is 2, $R^1$ is preferably —$CH_2CH(OH)CH_2$—. In a case where the number of n in the formula (1) is 2, the number of hydroxyl groups in the fluorine-containing ether compound that are derived from the terminal group represented by $R^3$ becomes four. Therefore, compared with a case where the number of n in the formula (1) is 3, the number of hydroxyl groups derived from the terminal group represented by $R^3$ becomes smaller by two. The hydroxyl groups in the fluorine-containing ether compound contribute to improvement in the adhesion between a lubricating layer containing the fluorine-containing ether compound and a protective layer. For example, when the number of n in the formula (1) is 2, both $R^1$'s that are included in the two substituents (—[O—$R^1$—O—$CH_2$—$R^2$—$CH_2$—$R^3$]) are —$CH_2CH(OH)CH_2$—. In this case, the number of hydroxyl groups in the fluorine-containing ether compound becomes a total of six, as two hydroxyl groups are derived from $R^1$ and four hydroxyl groups are derived from the terminal group represented by $R^3$. As a result, since the number of n is 2, even when the number of hydroxyl groups derived from the terminal group represented by $R^3$ is small compared with a case where the number of n is 3, the adhesion between a lubricating layer containing the fluorine-containing ether compound and a protective layer becomes favorable, which is preferable.

In the fluorine-containing ether compound of the present embodiment represented by the formula (1), $R^2$ is the perfluoropolyether chain (PFPE chain). $R^2$'s that the two or three substituents that are included in the fluorine-containing ether compound represented by the formula (1) each have may be different from each other, or some of $R^2$'s may be the same as each other, but $R^2$'s are preferably all the same as each other.

$R^2$ is not particularly limited and can be appropriately selected depending on performance or the like required for lubricants containing the fluorine-containing ether compound.

$R^2$ is preferably represented by any one of the following formula (2) to formula (4). In a case where $R^2$ is represented by any one of the formula (2) to formula (4), the synthesis of the fluorine-containing ether compound is easy, which is preferable.

In addition, in a case where $R^2$ is represented by any one of the formula (2) to formula (4), the ratio of the number of oxygen atoms (the number of ether bonds (—O—)) to the number of carbon atoms in the perfluoropolyether chain is appropriate. Therefore, the fluorine-containing ether compound becomes a compound with appropriate hardness. Therefore, the fluorine-containing ether compound applied onto a protective layer is less likely to be aggregated on the protective layer, and it is possible to form a lubricating layer having a thinner thickness at a sufficient coating rate. In addition, in a case where $R^2$ is represented by any one of the formula (2) to formula (4), the fluorine-containing ether compound becomes capable of providing lubricating layers having favorable wear resistance.

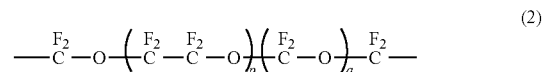

(2)

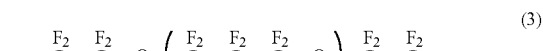

(3)

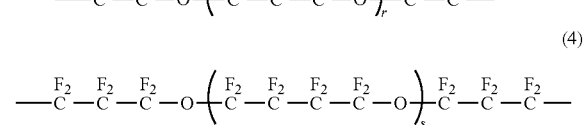

(4)

(In the formula (2), p represents 1 to 30, and q represents 0 to 30.)

(In the formula (3), r represents 1 to 30.)

(In the formula (4), s represents 1 to 20.)

In the formula (2), the arrangement sequence of ($CF_2$—$CF_2$—O) and ($CF_2$—O), which are repeating units, is not particularly limited. In the formula (2), the number p of ($CF_2$—$CF_2$—O)'s and the number q of ($CF_2$—O)'s may be the same as each other or may be different from each other. The formula (2) may include any one of a random copolymer, a block copolymer and an alternating copolymer composed of the monomer units ($CF_2$—$CF_2$—O) and ($CF_2$—O).

In a case where $R^2$ in the formula (1) is the formula (2), p that indicates the average degree of polymerization is 1 to 30, preferably 1 to 15 and more preferably 1 to 7. p may be 1 to 6 or 2 to 5. In a case where $R^2$ in the formula (1) is the formula (2), q that indicates the average degree of polymerization is 0 to 30, preferably 0 to 15 and more preferably 0 to 7. q may be 1 to 6 or 2 to 5. In addition, in a case where q is 0, p is preferably 1 to 10.

In a case where r that indicates the average degree of polymerization is 1 to 30 in the formula (3), the number-average molecular weight of the fluorine-containing ether compound of the present embodiment is likely to be within a preferable range. r is preferably 1 to 10 and more preferably 1 to 5.

In a case where s that indicates the average degree of polymerization is 1 to 20 in the formula (4), the number-average molecular weight of the fluorine-containing ether compound of the present embodiment is likely to be within a preferable range. s is preferably 1 to 10 and more preferably 1 to 5.

In the formula (1), $R^3$ is —$OCH_2CH(OH)CH_2$ $O(CH_2)_mOH$ (m in the formula is an integer of 2 to 4). m is an integer of 2 to 4 and preferably 2.

The fluorine-containing ether compound represented by the formula (1) is, specifically, preferably any one of the compounds represented by the formulae (A) to (N). $R^2$'s in the following formulae (A) to (N) are represented by any one of the formula (2) to formula (4), and the above-described preferable conditions regarding the formula (2) to formula (4) are also preferable for $R^2$'s in the following formulae (A) to (N) in the same manner.

p, q, r and s that are included in $R^2$'s in the formulae (A) to (N) are all values indicating the average degree of polymerization and thus are not necessarily integers. In a case where $R^2$ is the formula (2), p in the formula (2) represents 1 to 30, and q represents 0 to 30. In a case where $R^2$ is the formula (3), r in the formula (3) represents 1 to 30. In a case where $R^2$ is the formula (4), s in the formula (4) represents 1 to 20. In the compounds represented by the formulae (A) to (N), the two or three substituents bonding to the benzene ring are all the same as each other.

In the compound represented by the formula (A), n is 2, $R^1$ is —$CH_2CH(OH)CH_2$—, $R^2$ is the formula (2), and m in $R^3$ is 2.

In the compound represented by the formula (B), n is 2, $R^1$ is —$CH_2CH(OH)CH_2$, $R^2$ is the formula (3), and m in $R^3$ is 2.

In the compound represented by the formula (C), n is 2, $R^1$ is —$CH_2CH(OH)CH_2$—, $R^2$ is the formula (4), and m in $R^3$ is 2.

In the compound represented by the formula (D), n is 2, $R^1$ is —$CH_2CH(OH)CH_2$—, $R^2$ is the formula (2), and m in $R^3$ is 3.

In the compound represented by the formula (E), n is 2, $R^1$ is —$CH_2CH(OH)CH_2$—, $R^2$ is the formula (2), and m in $R^3$ is 4.

In the compound represented by the formula (F), n is 2, $R^1$ is —$CH_2CH_2$—, $R^2$ is the formula (2), and m in $R^3$ is 2.

In the compound represented by the formula (G), n is 2, $R^1$ is —$CH_2CH_2$—, $R^2$ is the formula (3), and m in $R^3$ is 2.

In the compound represented by the formula (H), n is 2, $R^1$ is —$CH_2CH_2$—, $R^2$ is the formula (4), and m in $R^3$ is 2.

In the compound represented by the formula (I), n is 3, $R^1$ is —$CH_2CH(OH)CH_2$—, $R^2$ is the formula (2), and m in $R^3$ is 2.

In the compound represented by the formula (J), n is 3, $R^1$ is —$CH_2CH_2CH_2$—, $R^2$ is the formula (2), and m in $R^3$ is 2.

In the compound represented by the formula (K), n is 3, $R^1$ is —$CH_2CH_2CH_2$—, $R^2$ is the formula (3), and m in $R^3$ is 2.

In the compound represented by the formula (L), n is 3, $R^1$ is —$CH_2CH_2CH_2$—, $R^2$ is the formula (4), and m in $R^3$ is 2.

In the compound represented by the formula (M), n is 3, $R^1$ is —$CH_2CH_2CH_2$—, $R^2$ is the formula (2), and m in $R^3$ is 3.

In the compound represented by the formula (N), n is 3, $R^1$ is —$CH_2CH_2CH_2$—, $R^2$ is the formula (2), and m in $R^3$ is 4.

(A)
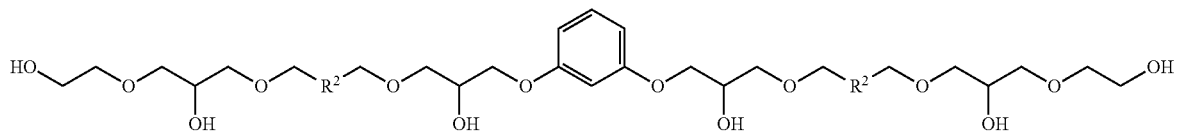

(B)
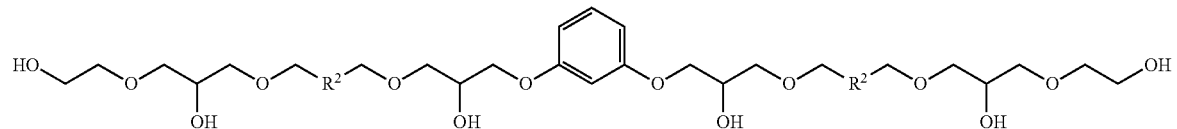

(C)
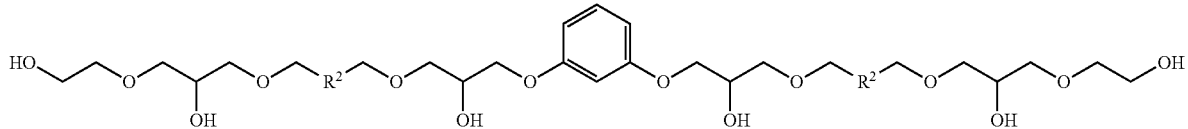

(D)
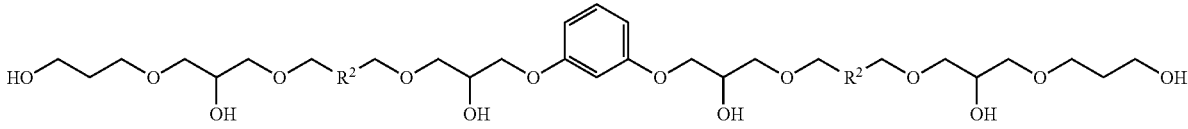

(E)
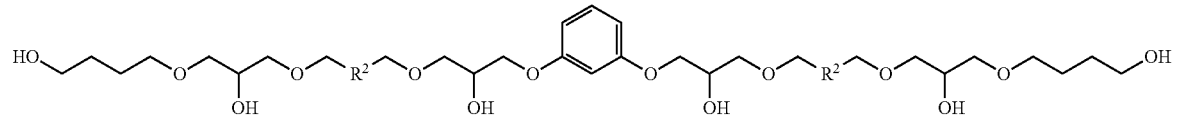

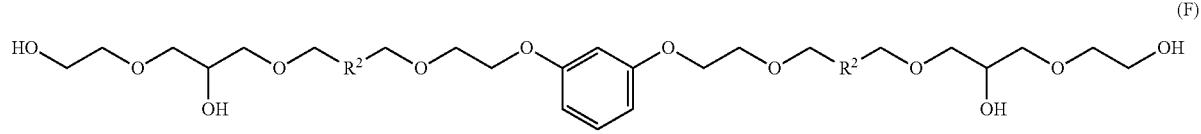

(F)

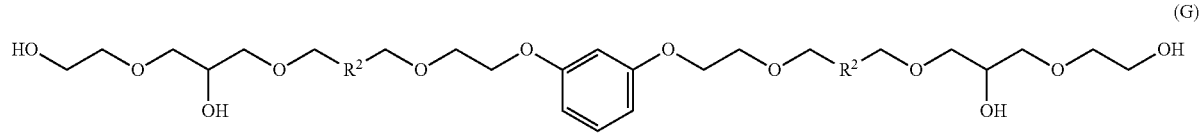

(G)

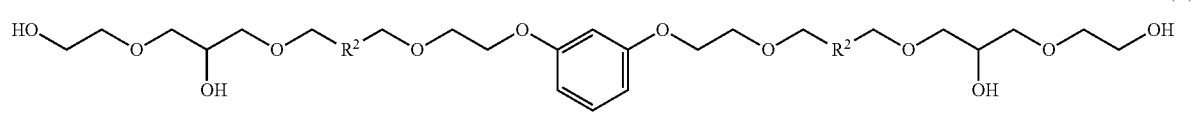

(H)

(In the formula (A), R² is represented by the formula (2).)
(In the formula (B), R² is represented by the formula (3).)
(In the formula (C), R² is represented by the formula (4).)
(In the formula (D), R² is represented by the formula (2).)

(In the formula (E), R² is represented by the formula (2).)
(In the formula (F), R² is represented by the formula (2).)
(In the formula (G), R² is represented by the formula (3).)
(In the formula (H), R² is represented by the formula (4).)

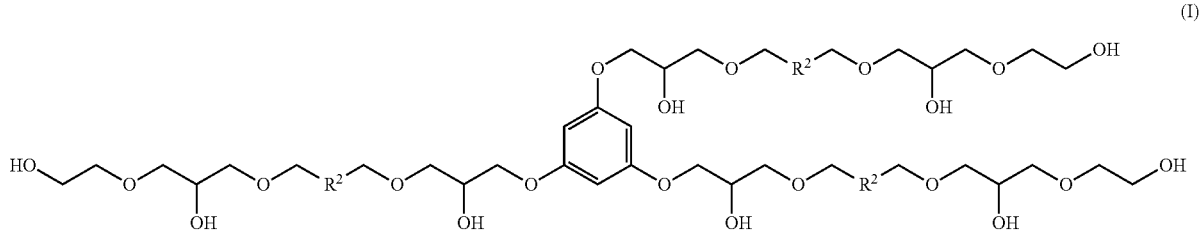

(I)

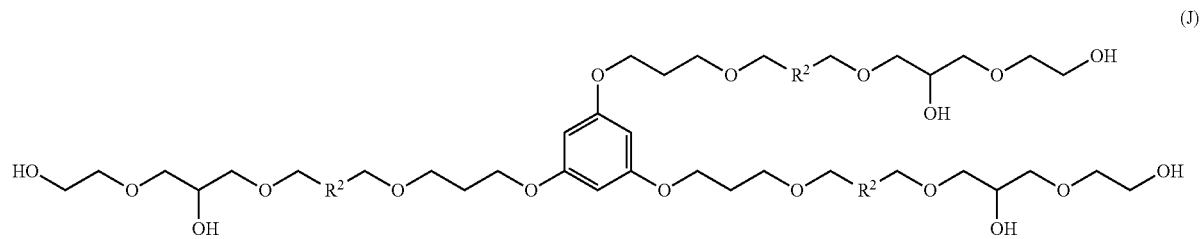

(J)

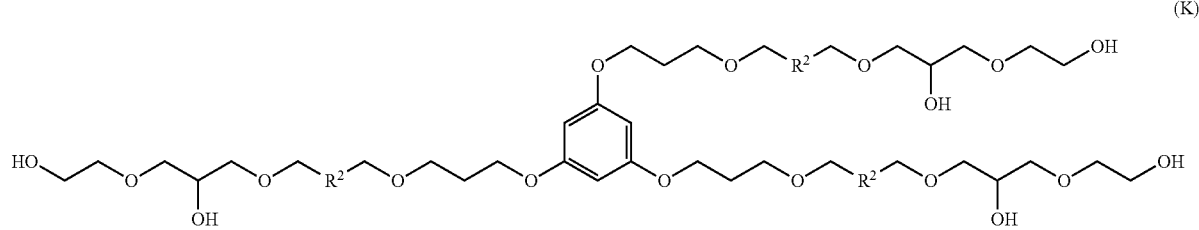

(K)

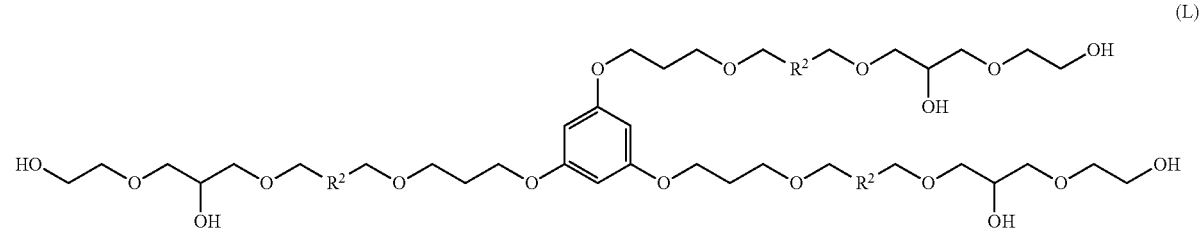

(L)

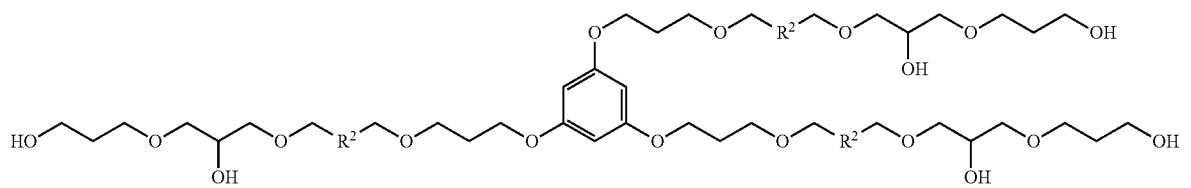

(M)

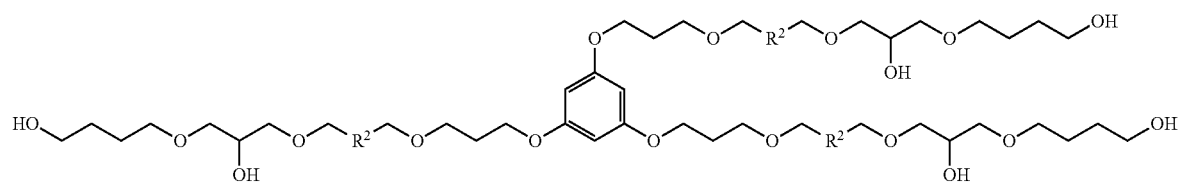

(N)

(In the formula (I), $R^2$ is represented by the formula (2).)
(In the formula (J), $R^2$ is represented by the formula (2).)
(In the formula (K), $R^2$ is represented by the formula (3).)
(In the formula (L), $R^2$ is represented by the formula (4).)
(In the formula (M), $R^2$ is represented by the formula (2).)
(In the formula (N), $R^2$ is represented by the formula (2).)

When the compound represented by the formula (1) is any one of the compounds represented by the formulae (A) to (N), the procurement of a raw material is easy, and furthermore, it is possible to form lubricating layers in which wear resistance is more excellent and pickup is further suppressed in spite of a thin thickness, which is preferable.

The number-average molecular weight (Mn) of the fluorine-containing ether compound of the present embodiment is preferably within a range of 500 to 10000. When the number-average molecular weight is 500 or more, lubricants containing the fluorine-containing ether compound of the present embodiment are less likely to evaporate, and it is possible to prevent lubricants from evaporating and being transferred to a magnetic head. The number-average molecular weight of the fluorine-containing ether compound is more preferably 1000 or more. In addition, when the number-average molecular weight is 10000 or less, the viscosity of the fluorine-containing ether compound becomes appropriate, and it is possible to easily form a lubricating layer having a thin thickness by applying a lubricant containing the fluorine-containing ether compound. The number-average molecular weight of the fluorine-containing ether compound is preferably 3000 or less in order to obtain a viscosity at which lubricants to which the fluorine-containing ether compound is applied are easy to handle.

The number-average molecular weight (Mn) of the fluorine-containing ether compound is a value measured by $^1$H-NMR and $^{19}$F-NMR with AVANCE 111400 manufactured by Bruker BioSpin Group. In the nuclear magnetic resonance (NMR) measurement, a specimen is diluted with one of hexafluorobenzene, acetone-d, tetrahydrofuran-d and the like or a mixed solvent thereof and used in the measurement. As the reference of the $^{19}$F-NMR chemical shift, the peak of hexafluorobenzene was set to −164.7 ppm, and, as the reference of the $^1$H-NMR chemical shift, the peak of acetone was set to 2.2 ppm.

"Production Method"

A method for producing the fluorine-containing ether compound of the present embodiment is not particularly limited, and the fluorine-containing ether compound can be produced using a well-known conventional production method. The fluorine-containing ether compound of the present embodiment can be produced using, for example, a production method described below.

First, a compound having a perfluoropolyether chain corresponding to $R^2$ in the formula (1) is prepared, and an addition reaction is conducted to the compound with benzene in which two or three carbon atoms are substituted with two or three halogenated alkoxy groups or two or three glycidyloxy groups. This generates a compound represented by the formula (1-1).

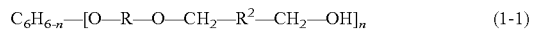

$$C_6H_{6-n}\text{—}[O\text{—}R\text{—}O\text{—}CH_2\text{—}R^2\text{—}CH_2\text{—}OH]_n \quad (1\text{-}1)$$

(in the formula (1-1), n is an integer of 2 or 3, $R^1$ is any one of —CH$_2$CH$_2$—, —CH$_2$CH$_2$CH$_2$— and —CH$_2$CH(OH)CH$_2$—, and $R^2$ is a perfluoropolyether chain.)

Examples of the benzene substituted with three halogenated alkoxy groups that is used at the time of producing the compound represented by the formula (1-1) include 1,3,5-tri(bromopropoxy)benzene, 1,2,3-tri(bromopropoxy)benzene, 1,2,4-tri(bromopropoxy)benzene, 1,3,5-tri(bromoethoxy)benzene, 1,2,3-tri(bromoethoxy)benzene, 1,2,4-tri(bromoethoxy)benzene and the like.

Examples of the benzene substituted with two halogenated alkoxy groups include o-di(bromopropoxy)benzene, m-di(bromopropoxy)benzene, p-di(bromopropoxy)benzene, o-di(bromoethoxy)benzene, m-di(bromoethoxy)benzene, p-di(bromoethoxy)benzene and the like.

The benzene substituted with two or three halogenated alkoxy groups can be obtained by, for example, causing an addition reaction between dihydroxybenzene or trihydroxybenzene and 1,3-dibromopropane or 1,2-dibromoethane.

Examples of the benzene substituted with three glycidyloxy groups that is used at the time of producing the compound represented by the formula (1-1) include 1,3,5-tri(glycidyloxy)benzene, 1,2,3-tri(glycidyloxy)benzene, 1,2,4-tri(glycidyloxy)benzene and the like.

Examples of the benzene substituted with two glycidyloxy groups include 1,3-bis(glycidyloxy)benzene, 1,2-bis(glycidyloxy)benzene, 1,4-bis(glycidyloxy)benzene and the like.

The benzene substituted with two or three glycidyloxy groups can be obtained by, for example, causing an addition reaction between dihydroxybenzene or trihydroxybenzene and epichlorohydrin or epibromohydrin.

Next, the compound represented by the formula (1-1) and epichlorohydrin or epibromohydrin are reacted to generate a perfluoropolyether in which the terminal hydrogen atoms in the two or three substituents (—[O—$R^1$—O—$CH_2$—$R^2$—$CH_2$—OH]) of the compound represented by the formula (1-1) are substituted with glycidyl groups. The generated perfluoropolyether is a compound in which two or three substituents having an epoxy group at the terminal bond to a benzene ring. Next, any compound selected from ethylene glycol, 1,3-propanediol and 1,4-butanediol and the perfluoropolyether generated by the above-described method are reacted with each other. A compound obtained as described above can be separated using, for example, a method in which column chromatography is used.

The fluorine-containing ether compound represented by the formula (1) can be obtained by the above-described method.

The fluorine-containing ether compound of the present embodiment is a compound represented by the formula (1). Therefore, when a lubricating layer is formed on a protective layer using a lubricant containing this fluorine-containing ether compound, the surface of the protective layer is coated with the PFPE chain represented by $R^2$ in the formula (1), and the friction force between a magnetic head and the protective layer is reduced. In addition, the lubricating layer formed using the lubricant containing the fluorine-containing ether compound of the present embodiment is excellent in terms of adhesion to the protective layer due to the intermolecular interaction of the benzene ring and/or the interaction between the benzene ring and the protective layer.

In addition, the lubricating layer containing the fluorine-containing ether compound of the present embodiment is closely attached onto the protective layer by bonds between the two hydroxyl groups that are included in each of the terminal groups represented by $R^3$ in the fluorine-containing ether compound and the protective layer. Furthermore, since the two hydroxyl groups that are included in the terminal group represented by $R^3$ bond to different carbon atoms, and the carbon atoms to which the hydroxyl groups bond bond to each other through a linking group including an oxygen atom, the lubricating layer containing the fluorine-containing ether compound of the present embodiment has favorable flexibility. Therefore, the lubricating layer containing the fluorine-containing ether compound of the present embodiment is easily adsorbed to the protective film and has excellent adhesion to the protective layer.

The above shows that, according to the fluorine-containing ether compound of the present embodiment, the lubricating layer and the protective layer are strongly bonded to each other, and a lubricating layer in which wear resistance is excellent and pickup is suppressed can be obtained.

[Lubricant for Magnetic Recording Medium]

A lubricant for a magnetic recording medium of the present embodiment contains the fluorine-containing ether compound represented by the formula (1).

The lubricant of the present embodiment can be used after being mixed as necessary with a well-known material that is used as a material for lubricants as long as characteristics attributed to the fluorine-containing ether compound represented by the formula (1) contained in the lubricant are not impaired.

Specific examples of the well-known material include FOMBLIN (registered trademark) ZDIAC, FOMBLIN ZDEAL, FOMBLIN AM-2001 (all manufactured by Solvay Solexis), Moresco A20H (manufactured by Moresco Corporation) and the like. The number-average molecular weight of the well-known material that is used by being mixed with the lubricant of the present embodiment is preferably 1000 to 10000.

In a case where the lubricant of the present embodiment contains a material other than the fluorine-containing ether compound represented by the formula (1), the content of the fluorine-containing ether compound represented by the formula (1) in the lubricant of the present embodiment is preferably 50 mass % or more, and more preferably 70 mass % or more. The content of the fluorine-containing ether compound may be 80 mass % or more, or 90 mass % or more. The upper limit can be arbitrarily selected and may be, for example, 99 mass % or less, 95 mass % or less, or 90 mass % or less.

The lubricant of the present embodiment contains the fluorine-containing ether compound represented by the formula (1) and is thus capable of coating the surface of protective layers at a high coating rate in spite of a thin thickness and enables the formation of lubricating layers having excellent adhesion to the protective layers. Therefore, according to the lubricant of the present embodiment, lubricating layers in which wear resistance is excellent and pickup is suppressed in spite of a thin thickness can be obtained.

[Magnetic Recording Medium]

A magnetic recording medium of the present embodiment has at least a magnetic layer, a protective layer and a lubricating layer sequentially provided on a substrate.

In the magnetic recording medium of the present embodiment, one or more underlayers can be provided as necessary between the substrate and the magnetic layer. In addition, it is also possible to provide an adhesive layer and/or a soft magnetic layer between the underlayer and the substrate.

FIG. 1 is a schematic cross-sectional view showing an embodiment of the magnetic recording medium of the present invention.

A magnetic recording medium 10 of the present embodiment has a structure in which an adhesive layer 12, a soft magnetic layer 13, a first underlayer 14, a second underlayer 15, a magnetic layer 16, a protective layer 17 and a lubricant layer 18 are sequentially provided on a substrate 11.

"Substrate"

As the substrate 11, for example, a non-magnetic substrate or the like in which a NiP or NiP alloy film is formed on a base made of a metal or alloy material such as Al or an Al alloy can be used.

In addition, as the substrate 11, a non-magnetic substrate made of a non-metal material such as glass, ceramic, silicon, silicon carbide, carbon or resin may be used or a non-magnetic substrate in which a NiP or NiP alloy film is formed on a base made of this non-metal material may be used.

"Adhesive layer"

The adhesive layer 12 prevents the progress of corrosion of the substrate 11 which may occur in a case where the substrate 11 and the soft magnetic layer 13, which is provided on the adhesive layer 12, are disposed in contact with each other.

The material of the adhesive layer 12 can be appropriately selected from, for example, Cr, a Cr alloy, Ti, a Ti alloy, CrTi, NiAl, an AlRu alloy and the like. The adhesive layer 12 can be formed by, for example, a sputtering method.

"Soft Magnetic Layer"

The soft magnetic layer 13 preferably has a structure in which a first soft magnetic film, an interlayer made of a Ru film and a second soft magnetic film are sequentially laminated. That is, the soft magnetic layer 13 preferably has a structure in which the interlayer made of a Ru film is sandwiched between the two soft magnetic films and thereby the soft magnetic films on and under the interlayer are antiferromagnetically coupled (AFC).

Examples of the material of the first soft magnetic film and the second soft magnetic film include a CoZrTa alloy, a CoFe alloy and the like.

To the CoFe alloy that is used for the first soft magnetic film and the second soft magnetic film, any of Zr, Ta and Nb is preferably added. This accelerates the amorphization of the first soft magnetic film and the second soft magnetic film, makes it possible to improve the orientation of the first underlayer (seed layer) and makes it possible to reduce the flying height of a magnetic head.

The soft magnetic layer 13 can be formed by, for example, a sputtering method.

"First Underlayer"

The first underlayer 14 is a layer for controlling the orientations or crystal sizes of the second underlayer 15 and the magnetic layer 16 that are provided on the first underlayer 14.

Examples of the first underlayer 14 include a Cr layer, a Ta layer, a Ru layer, layers of an alloy such as CrMo, CoW, CrW, CrV or CrTi, and the like.

The first underlayer 14 can be formed by, for example, a sputtering method.

"Second Underlayer"

The second underlayer 15 is a layer that controls the orientation of the magnetic layer 16 to be favorable. The second underlayer 15 is preferably a Ru or Ru alloy layer.

The second underlayer 15 may be a single layer or may be composed of a plurality of layers. In a case where the second underlayer 15 is composed of a plurality of layers, all of the layers may be composed of the same material or at least one layer thereof may be composed of a different material.

The second underlayer 15 can be formed by, for example, a sputtering method.

"Magnetic Layer"

The magnetic layer 16 is made of a magnetic film in which the easy magnetization axis is directed in a direction perpendicular or parallel to the surface of the substrate. The magnetic layer 16 is, for example, a layer containing Co and Pt and may be a layer further containing an oxide, Cr, B, Cu, Ta, Zr or the like in order to improve SNR characteristics.

Examples of the oxide that is contained in the magnetic layer 16 include $SiO_2$, SiO, $Cr_2O_3$, CoO, $Ta_2O_3$, $TiO_2$ and the like.

The magnetic layer 16 may be composed of a single layer or may be composed of a plurality of magnetic layers made of materials having different compositions.

For example, in a case where the magnetic layer 16 is composed of three layers of a first magnetic layer, a second magnetic layer and a third magnetic layer sequentially laminated from below, the first magnetic layer is preferably a granular structure made of a material containing Co, Cr and Pt and further containing an oxide. As the oxide that is contained in the first magnetic layer, for example, oxides of Cr, Si, Ta, Al, Ti, Mg, Co or the like are preferably used. Among them, in particular, $TiO_2$, $Cr_2O_3$, $SiO_2$ and the like can be preferably used. In addition, the first magnetic layer is preferably made of a composite oxide in which two or more oxides are added. Among them, in particular, $Cr_2O_3$—$SiO_2$, $Cr_2O_3$—$TiO_2$, $SiO_2$—$TiO_2$ and the like can be preferably used.

The first magnetic layer may preferably contain, in addition to Co, Cr, Pt and the oxide, one or more elements selected from B, Ta, Mo, Cu, Nd, W, Nb, Sm, Tb, Ru and Re.

For the second magnetic layer, the same material as for the first magnetic layer can be used. The second magnetic layer is preferably a granular structure.

The third magnetic layer is preferably a non-granular structure made of a material containing Co, Cr and Pt but containing no oxides. The third magnetic layer may preferably contain, in addition to Co, Cr, and Pt, one or more elements selected from B, Ta, Mo, Cu, Nd, W, Nb, Sm, Tb, Ru, Re and Mn.

In a case where the magnetic layer 16 is formed of a plurality of magnetic layers, a non-magnetic layer is preferably provided between the magnetic layers adjacent to each other. In a case where the magnetic layer 16 is made up of three layers of the first magnetic layer, the second magnetic layer and the third magnetic layer, it is preferable to provide a non-magnetic layer between the first magnetic layer and the second magnetic layer and a non-magnetic layer between the second magnetic layer and the third magnetic layer.

For the non-magnetic layer that is provided between the magnetic layers adjacent to each other in the magnetic layer 16, it is possible to preferably use, for example, Ru, a Ru alloy, a CoCr alloy, a CoCrX1 alloy (X1 represents one or more elements selected from Pt, Ta, Zr, Re, Ru, Cu, Nb, Ni, Mn, Ge, Si, O, N, W, Mo, Ti, V and B) and the like.

For the non-magnetic layer that is provided between the magnetic layers adjacent to each other in the magnetic layer 16, an alloy material containing an oxide, a metallic nitride or a metallic carbide is preferably used. Specifically, as the oxide, for example, $SiO_2$, $Al_2O_3$, $Ta_2O_5$, $Cr_2O_3$, MgO, $Y_2O_3$, $TiO_2$ and the like can be preferably used. As the metallic nitride, for example, AlN, $Si_3N_4$, TaN, CrN and the like can be preferably used. As the metallic carbide, for example, TaC, BC, SiC and the like can be preferably used.

The non-magnetic layer can be formed by, for example, a sputtering method.

The magnetic layer 16 is preferably a magnetic layer for perpendicular magnetic recording in which the easy magnetization axis is directed in a direction perpendicular to the surface of the substrate in order to realize a higher recording density. The magnetic layer 16 may be a magnetic layer for longitudinal magnetic recording.

The magnetic layer 16 may be formed by any well-known conventional method such as a deposition method, an ion beam sputtering method or a magnetron sputtering method. The magnetic layer 16 is normally formed by a sputtering method.

"Protective Layer"

The protective layer 17 protects the magnetic layer 16. The protective layer 17 may be composed of a single layer or may be composed of a plurality of layers. Examples of the material of the protective layer 17 include carbon, nitrogen-containing carbon, silicon carbide and the like.

As the protective layer 17, a carbon-based protective layer can be preferably used, and, in particular, an amorphous carbon protective layer is preferable. When the protective layer 17 is a carbon-based protective layer, the interaction with the hydroxyl group that is included in the fluorine-containing ether compound in the lubricating layer 18 is further enhanced, which is preferable.

The adhesive force between the carbon-based protective layer and the lubricating layer 18 can be controlled by forming the carbon-based protective layer with hydrogenated carbon and/or nitrogenated carbon and adjusting the hydrogen content and/or the nitrogen content in the carbon-based protective layer. The hydrogen content in the carbon-based protective layer is preferably 3 to 20 atomic % when measured by the hydrogen forward scattering method (HFS). In addition, the nitrogen content in the carbon-based protective layer is preferably 4 to 15 atomic % when measured by X-ray photoelectron spectroscopy (XPS).

The hydrogen and/or nitrogen that are contained in the carbon-based protective layer do not need to be uniformly contained throughout the entire carbon-based protective layer. The carbon-based protective layer is preferably formed as a composition gradient layer in which nitrogen is contained in the lubricating layer 18 side of the protective layer 17 and hydrogen is contained in the magnetic layer 16 side of the protective layer 17. In this case, the adhesive force between the magnetic layer 16 and the carbon-based protective layer and the adhesive force between the lubricating layer 18 and the carbon-based protective layer further improve.

The film thickness of the protective layer 17 can be arbitrarily selected, but is preferably set to 1 nm to 7 nm. When the film thickness of the protective layer 17 is 1 nm or more, performance as the protective layer 17 can be sufficiently obtained. The film thickness of the protective layer 17 is preferably 7 nm or less from the viewpoint of reducing the thickness of the protective layer 17.

As a method for forming the protective layer 17, it is possible to use a sputtering method in which a carbon-containing target material is used, a chemical vapor deposition (CVD) method in which a hydrocarbon raw material such as ethylene or toluene is used, an ion beam deposition (IBD) method and the like.

In the case of forming a carbon-based protective layer as the protective layer 17, the carbon-based protective layer can be formed by, for example, a DC magnetron sputtering method. Particularly, in the case of forming a carbon-based protective layer as the protective layer 17, an amorphous carbon protective layer is preferably formed by a plasma CVD method. The amorphous carbon protective layer formed by the plasma CVD method has a uniform surface with small roughness.

"Lubricating Layer"

The lubricating layer 18 prevents the contamination of the magnetic recording medium 10. In addition, the lubricating layer 18 reduces the friction force of a magnetic head of a magnetic recording/reproducing device, which slides on the magnetic recording medium 10, and thereby improves the durability of the magnetic recording medium 10.

The lubricating layer 18 is formed in contact with the protective layer 17 as shown in FIG. 1. The lubricating layer 18 contains the above-described fluorine-containing ether compound.

In a case where the protective layer 17, which is disposed below the lubricating layer 18, is a carbon-based protective layer, the lubricating layer 18 is bonded to the protective layer 17 with a particularly high bonding force. As a result, it becomes easy to obtain the magnetic recording medium 10 in which the surface of the protective layer 17 is coated with the lubricating layer 18 at a high coating rate in spite of a thin thickness, and it is possible to effectively prevent the contamination on the surface of the magnetic recording medium 10.

The average film thickness of the lubricating layer 18 can be arbitrarily selected, but is preferably 0.5 nm (5 Å) to 3 nm (30 Å) and more preferably 0.5 nm (5 Å) to 1 nm (10 Å). When the average film thickness of the lubricating layer 18 is 0.5 nm or more, the lubricating layer 18 does not become an island shape or a mesh shape and is formed in a uniform film thickness. Therefore, the surface of the protective layer 17 can be coated with the lubricating layer 18 at a high coating rate. In addition, when the average film thickness of the lubricating layer 18 is 3 nm or less, it is possible to sufficiently reduce the thickness of the lubricating layer 18 and to sufficiently decrease the flying height of a magnetic head.

In a case where the surface of the protective layer 17 is not sufficiently coated with the lubricating layer 18 at a high coating rate, an environmental substance adsorbed to the surface of the magnetic recording medium 10 passes through voids in the lubricating layer 18 and intrudes below the lubricating layer 18. The environmental substance that has intruded below the lubricating layer 18 is adsorbed and bonded to the protective layer 17 and generates a contamination substance. In addition, at the time of reproducing magnetic records, this contamination substance (aggregation component) is attached (transferred) to a magnetic head as a smear to break the magnetic head or degrade the magnetic recording/reproducing characteristics of magnetic recording/reproducing devices.

Examples of the environmental substance that generates the contamination substance include siloxane compounds (cyclic siloxane and linear siloxane), ionic impurities, hydrocarbons having a relatively high molecular weight such as octacosane, plasticizers such as dioctyl phthalate and the like. Examples of a metal ion that is contained in the ionic impurities include a sodium ion, a potassium ion and the like. Examples of an inorganic ion that is contained in the ionic impurities include a chlorine ion, a bromine ion, a nitrate ion, a sulfate ion, an ammonium ion and the like. Examples of an organic ion that is contained in the ionic impurities include an oxalate ion, a formate ion and the like.

"Method for Forming Lubricating Layer"

A method for forming the lubricating layer 18 can be arbitrarily selected and is, for example, a method in which a magnetic recording medium that is not yet fully manufactured and thus includes the individual layers up to the protective layer 17 formed on the substrate 11 is prepared and a solution for forming the lubricating layer is applied and dried on the protective layer 17.

The solution for forming the lubricating layer can be obtained by, for example, dispersing and dissolving the above-described lubricant for a magnetic recording medium of the embodiment in a solvent as necessary and adjusting the viscosity and concentration to be suitable for application methods.

Examples of the solvent that is used for the solution for forming the lubricating layer include fluorine-based solvents such as VERTREL (registered trademark) XF (trade name, manufactured by Dupont-Mitsui Fluorochemicals Co., Ltd.) and the like.

A method for applying the solution for forming the lubricating layer is not particularly limited, and examples thereof include a spin coating method, a spraying method, a paper coating method, a dipping method and the like.

In the case of using the dipping method, it is possible to use, for example, a method described below. First, the substrate 11 on which the individual layers up to the protective layer 17 have been formed is immersed into the solution for forming the lubricating layer that has been put into an immersion vessel of a dip coater. Next, the substrate 11 is lifted from the immersion vessel at a predetermined speed. This applies the solution for forming the lubricating layer to the surface on the protective layer 17 of the substrate 11.

The use of the dipping method makes it possible to uniformly apply the solution for forming the lubricating layer to the surface of the protective layer 17 and makes it possible to form the lubricating layer 18 on the protective layer 17 in a uniform film thickness.

In the present embodiment, a thermal treatment is preferably carried out on the substrate 11 on which the lubricating layer 18 has been formed. The thermal treatment improves the adhesion between the lubricating layer 18 and the protective layer 17 and improves the adhesive force between the lubricating layer 18 and the protective layer 17.

The thermal treatment temperature can be arbitrarily selected, but is preferably set to 100° C. to 180° C. When the thermal treatment temperature is 100° C. or higher, an effect on improvement in the adhesion between the lubricating layer 18 and the protective layer 17 can be sufficiently obtained. In addition, when the thermal treatment temperature is set to 180° C. or lower, it is possible to prevent the thermal decomposition of the lubricating layer 18. The thermal treatment time is preferably set to 10 to 120 minutes.

In the present embodiment, a treatment in which the lubricating layer 18 on the substrate 11 before the thermal treatment or after the thermal treatment is irradiated with ultraviolet rays (UV) may be carried out in order to further improve the adhesive force of the lubricating layer 18 to the protective layer 17.

The magnetic recording medium 10 of the present embodiment has at least the magnetic layer 16, the protective layer 17 and the lubricating layer 18 sequentially provided on the substrate 11. In the magnetic recording medium 10 of the present embodiment, the lubricating layer 18 containing the above-described fluorine-containing ether compound is formed in contact with the protective layer 17. This lubricating layer 18 coats the surface of the protective layer 17 at a high coating rate in spite of a thin thickness. Therefore, in the magnetic recording medium 10 of the present embodiment, the intrusion of the environmental substance, which generates the contamination substance such as the ionic impurities, from voids in the lubricating layer 18 is prevented. Therefore, the amount of the contamination substance present on the surface of the magnetic recording medium 10 of the present embodiment is small. In addition, in the lubricating layer 18 in the magnetic recording medium 10 of the present embodiment, foreign matter (smear) is less likely to be generated, and pickup can be suppressed. In addition, the lubricating layer 18 in the magnetic recording medium 10 of the present embodiment has excellent wear resistance. Therefore, the magnetic recording medium 10 of the present embodiment has excellent reliability and durability.

EXAMPLES

Hereinafter, the present invention will be more specifically described using examples and comparative examples. The present invention is not limited only to the following examples.

Example 1

A compound represented by the following formula (5) was produced by a method described below.

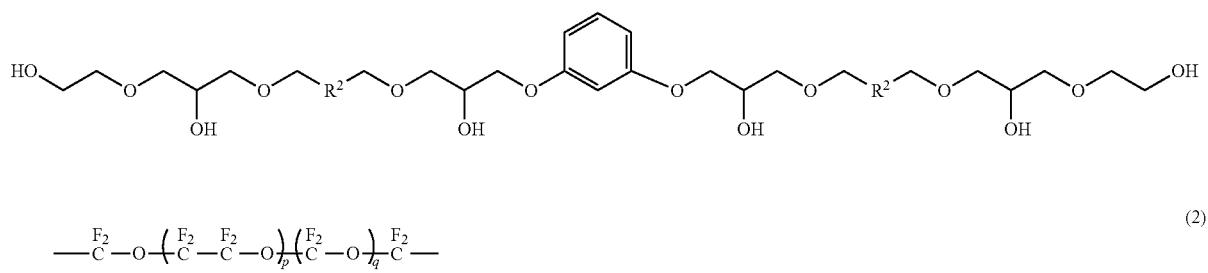

(5)

(2)

(In the formula (5), $R^2$ is represented by the following formula (2).)

(In the formula (2), p is 3.0 and q is 3.0.)

1,3-Dihydroxybenzene and epichlorohydrin were used and reacted in an acetone solvent in the presence of potassium carbonate, thereby synthesizing a compound represented by the following formula (6).

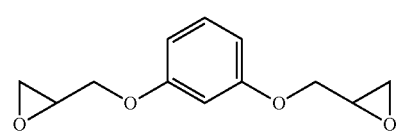

(6)

In addition, a compound represented by $HOCH_2CF_2O(CF_2CF_2O)_p(CF_2O)_qCF_2CH_2OH$ (in the formula, q is 3.0 and q is 3.0) (number-average molecular weight: 650, molecular weight distribution: 1.1) (30.0 g), a compound represented by the formula (6) (molecular weight: 222, 6.1 mmol) (1.35 g) and t-butanol (t-BuOH) (20 mL) were charged into a 100 mL eggplant flask in a nitrogen gas atmosphere and stirred at room temperature until the components became homogeneous. Potassium tert-butoxide (t-BuOK) (0.50 g, molecular weight: 112, 4.5 mmol) was further added to this uniform liquid and reacted by being stirred at 70° C. for 16 hours.

The obtained reaction product was cooled to 25° C., moved to a separatory funnel containing water (40 mL) and extracted twice using ethyl acetate (100 mL). An organic layer was washed with water and dehydrated with anhydrous sodium sulfate. The drying agent was filtered, the filtrate was then concentrated, and the residue was purified by silica gel column chromatography, thereby obtaining a compound represented by the following formula (7) (7.6 g) (number-average molecular weight: 1669, 4.6 mmol).

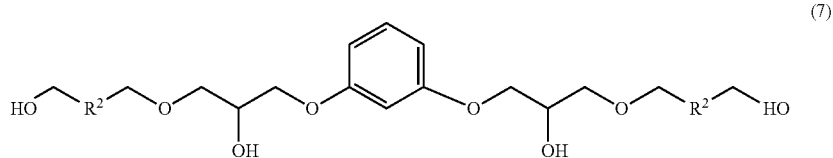

(7)

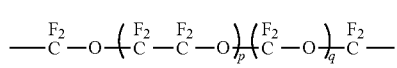

(2)

(In the formula (7), $R^2$ is represented by the following formula (2).)

(In the formula (2), p is 3.0 and q is 3.0.)

Next, the compound represented by the formula (7) (7.5 g), epibromohydrin (1.25 g) (molecular weight: 137, 9.1 mmol) and t-BuOH (25 mL) were charged and stirred at room temperature until the components became homogeneous. t-BuOK (1.00 g) (molecular weight: 112, 8.9 mmol) was added to this homogeneous liquid and stirred at 70° C. for 6 hours to be reacted.

The obtained reaction product was cooled to 25° C., moved to a separatory funnel containing water (30 mL) and extracted twice with ethyl acetate (100 mL). An organic layer was washed with water and dehydrated with anhydrous sodium sulfate. The drying agent was filtered, the filtrate was then concentrated, and the residue was purified by silica gel column chromatography, thereby obtaining a compound represented by the following formula (8) (6.3 g) (number-average molecular weight: 1781, 3.5 mmol).

neous. t-BuOK (0.40 g) (molecular weight: 112, 3.6 mmol) was added to this homogeneous liquid and stirred at 70° C. for 6 hours to be reacted.

The obtained reaction product was cooled to 25° C., moved to a separatory funnel containing water (30 mL) and extracted twice with ethyl acetate (100 mL). An organic layer was washed with water and dehydrated with anhydrous sodium sulfate. The drying agent was filtered, the filtrate was then concentrated, and the residue was purified by silica gel column chromatography, thereby obtaining a compound represented by the above-described formula (5) (4.3 g).

$^1$H-NMR and $^{19}$F-NMR measurements were carried out on the obtained compound (5), and the structure was identified from the following results.

(Identification Data)

$^1$H-NMR (acetone-$D_6$): δ [ppm] 3.3 to 4.2 (36H), 6.6 to 6.8 (4H)

$^{19}$F-NMR (acetone-$D_6$): δ [ppm]=−55.5 to −51.5 (12F), −78.5 (4F), −80.5 (4F), −91.0 to −88.5 (24F)

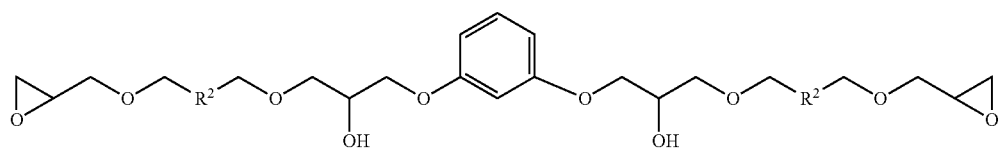

(8)

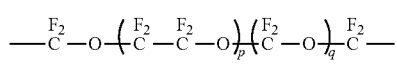

(2)

(In the formula (8), $R^2$ is represented by the following formula (2).)

(In the formula (2), p is 3.0 and q is 3.0.)

Next, the compound represented by the formula (8) (6.0 g), ethylene glycol (1.67 g) (molecular weight: 62, 0.26.9 mmol) and t-BuOH (30 mL) were charged and stirred at room temperature until the components became homoge- Example 2

A compound represented by the following formula (9) (4.4 g) was obtained in the same manner as in Example 1 except that fluoropolyether represented by $HOCH_2CF_2O(CF_2CF_2O)_p(CF_2O)_qCF_2CH_2OH$ (in the formula, p is 4.5 and q is 0) (number-average molecular weight: 650, molecular weight distribution: 1.2) was used in place of the fluoropolyether represented by $HOCH_2CF_2O(CF_2CF_2O)_p(CF_2O)_qCF_2CH_2OH$ (in the formula, p is 3.0 and q is 3.0) used in Example 1.

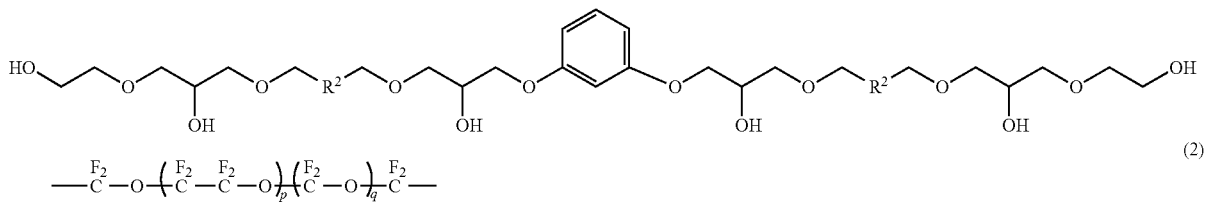

(9)

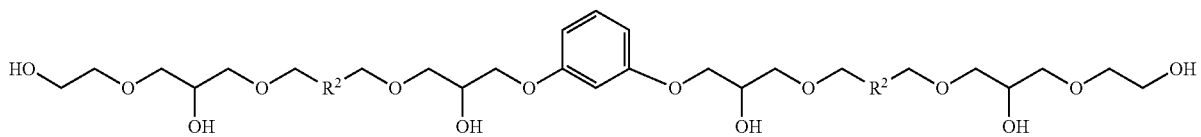

(2)

(In the formula (9), $R^2$ is represented by the following formula (2).)

(In the formula (2), p is 4.5 and q is 0.)

$^1$H-NMR and $^{19}$F-NMR measurements were carried out on the obtained compound (9), and the structure was identified from the following results.

(Identification Data)

$^1$H-NMR (acetone-$D_6$): δ [ppm] 3.3 to 4.2 (36H), 6.6 to 6.8 (4H)

$^{19}$F-NMR (acetone-$D_6$): δ [ppm]=−78.5 (4F), −81.3 (4F), −90.0 to −88.5 (36F)

Example 3

A compound represented by the following formula (10) (4.4 g) was obtained in the same manner as in Example 1 except that fluoropolyether represented by $HOCH_2CF_2CF_2O(CF_2CF_2CF_2O)CF_2CF_2CH_2OH$ (in the formula, r is 2.5.) (number-average molecular weight: 650, molecular weight distribution: 1.2) was used in place of the fluoropolyether represented by $HOCH_2CF_2O(CF_2CF_2O)_p(CF_2O)_qCF_2CH_2OH$ (in the formula, p is 3.0 and q is 3.0) used in Example 1.

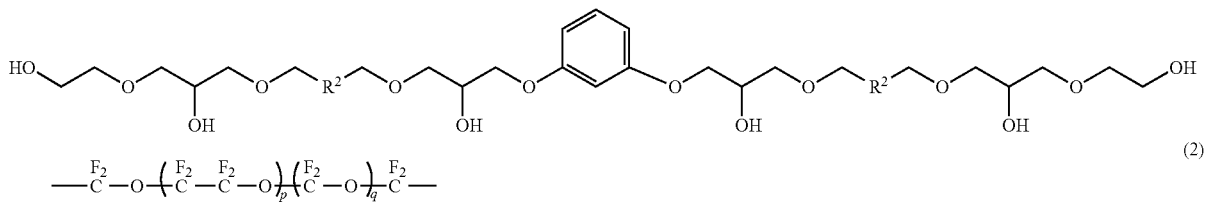

(10)

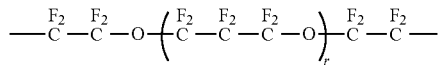

(3)

(In the formula (10), $R^2$ is represented by the following formula (3).)

(In the formula (3), r is 2.5.)

$^1$H-NMR and $^{19}$F-NMR measurements were carried out on the obtained compound (10), and the structure was identified from the following results.

(Identification Data)

$^1$H-NMR (acetone-$D_6$): δ [ppm] 3.3 to 4.2 (36H), 6.6 to 6.8 (4H)

$^{19}$F-NMR (acetone-$D_6$): δ [ppm]=−84.0 to −83.0 (20F), −86.4 (8F), −124.3 (8F), −130.0 to −129.0 (10F)

Example 4

A compound represented by the following formula (11) (3.9 g) was obtained in the same manner as in Example 1 except that fluoropolyether represented by $HOCH_2CF_2CF_2CF_2O(CF_2CF_2CF_2CF_2O)_s$ $CF_2CF_2CF_2CH_2OH$ (in the formula, s is 1.5.) (number-average molecular weight: 650, molecular weight distribution: 1.2) was used in place of the fluoropolyether represented by $HOCH_2CF_2O(CF_2CF_2O)_p(CF_2O)_qCF_2CH_2OH$ (in the formula, p is 3.0 and q is 3.0) used in Example 1.

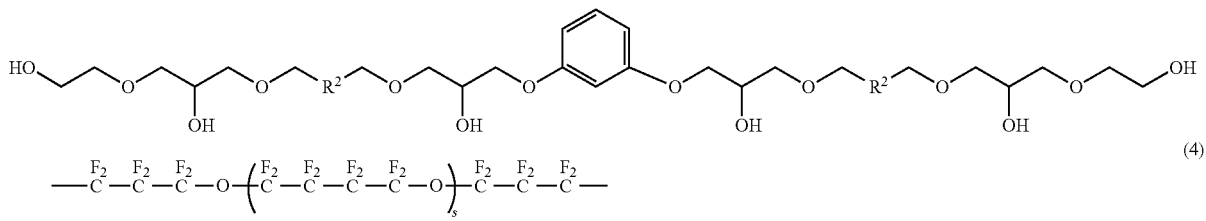

(In the formula (11), $R^2$ is represented by the following formula (4).)

(In the formula (4), s is 1.5.)

$^1$H-NMR and $^{19}$F-NMR measurements were carried out on the obtained compound (11), and the structure was identified from the following results.

(Identification Data)

$^1$H-NMR (acetone-$D_6$): δ [ppm] 3.3 to 4.2 (36H), 6.6 to 6.8 (4H)

$^{19}$F-NMR (acetone-$D_6$): δ [ppm]=−84.0 to −83.0 (20F), −122.5 (8F), −126.0 (12F), −129.0 to −128.0 (8F)

Example 5

A compound represented by the following formula (12) (4.5 g) was obtained in the same manner as in Example 1 except that 1,3-propanediol was used in place of ethylene glycol used in Example 1.

(In the formula (12), $R^2$ is represented by the following formula (2).)

(In the formula (2), p is 3.0 and q is 3.0.)

$^1$H-NMR and $^{19}$F-NMR measurements were carried out on the obtained compound (12), and the structure was identified from the following results.

(Identification Data)

$^1$H-NMR (acetone-$D_6$): δ [ppm] 1.00 to 1.40 (4H), 3.3 to 4.2 (36H), 6.6 to 6.8 (4H)

$^{19}$F-NMR (acetone-$D_6$): δ [ppm]=−55.5 to −51.5 (12F), −78.5 (4F), −80.5 (4F), −91.0 to −88.5 (24F)

Example 6

A compound represented by the following formula (13) (4.2 g) was obtained in the same manner as in Example 1 except that 1,4-butanediol was used in place of ethylene glycol used in Example 1.

(In the formula (13), $R^2$ is represented by the following formula (2).)

(In the formula (2), p is 3.0 and q is 3.0.)

$^1$H-NMR and $^{19}$F-NMR measurements were carried out on the obtained compound (13), and the structure was identified from the following results.

(Identification Data)

$^1$H-NMR (acetone-$D_6$): δ [ppm] 1.00 to 1.40 (8H), 3.3 to 4.2 (36H), 6.6 to 6.8 (4H)

$^{19}$F-NMR (acetone-$D_6$): δ [ppm]=−55.5 to −51.5 (12F), −78.5 (4F), −80.5 (4F), −91.0 to −88.5 (24F)

Example 7

A compound represented by the following formula (14) was synthesized by a method in which a substitution reaction was carried out using 1,3-dihydroxybenzene and 1,2-dibromoethane under a basic condition.

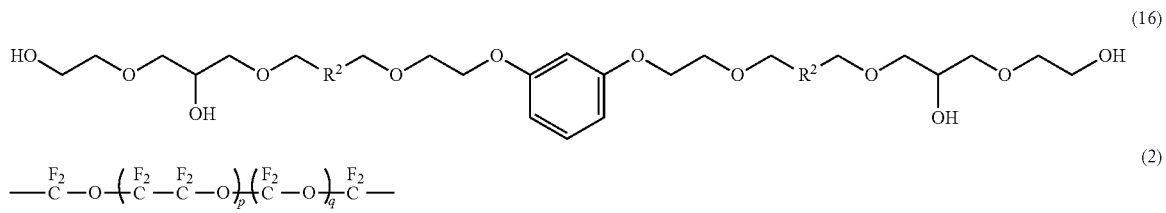

(14)

In addition, a compound represented by the following formula (15) (3.8 g) was obtained in the same manner as in Example 1 except that the compound represented by the formula (14) was used in place of the compound represented by the formula (6) used in Example 1.

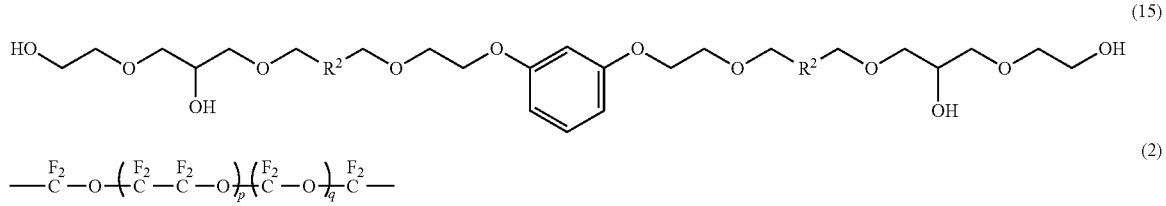

(In the formula (15), $R^2$ is represented by the following formula (2).)

(In the formula (2), p is 3.0 and q is 3.0.)

$^1$H-NMR and $^{19}$F-NMR measurements were carried out on the obtained compound (15), and the structure was identified from the following results.

(Identification Data)

$^1$H-NMR (acetone-$D_6$): δ [ppm] 3.3 to 4.2 (34H), 6.6 to 6.8 (4H)

$^{19}$F-NMR (acetone-$D_6$): δ [ppm]=−55.5 to −51.5 (12F), −78.5 (4F), −80.5 (4F), −91.0 to −88.5 (24F)

Example 8

A compound represented by the following formula (16) (3.9 g) was obtained in the same manner as in Example 1 except that fluoropolyether represented by $HOCH_2CF_2O(CF_2CF_2O)_p(CF_2O)_qCF_2CH_2OH$ (in the formula, p is 4.5 and q is 0) (number-average molecular weight: 650, molecular weight distribution: 1.2) was used in place of the fluoropolyether represented by $HOCH_2CF_2O(CF_2CF_2O)_p(CF_2O)_qCF_2CH_2OH$ (in the formula, p is 3.0 and q is 3.0) used in Example 1, and the compound represented by the formula (14) was used in place of the compound represented by the formula (6).

(16)

(In the formula (16), $R^2$ is represented by the following formula (2).)

(In the formula (2), p is 4.5 and q is 0.)

$^1$H-NMR and $^{19}$F-NMR measurements were carried out on the obtained compound (16), and the structure was identified from the following results.

(Identification Data)

$^1$H-NMR (acetone-$D_6$): δ [ppm] 3.3 to 4.2 (34H), 6.6 to 6.8 (4H)

$^{19}$F-NMR (acetone-$D_6$): δ [ppm]=−78.5 (4F), −81.3 (4F), −90.0 to −88.5 (36F)

Example 9

A compound represented by the following formula (17) (3.9 g) was obtained in the same manner as in Example 1 except that fluoropolyether represented by $HOCH_2CF_2CF_2O(CF_2CF_2CF_2O)_rCF_2CF_2CH_2OH$ (in the formula, r is 2.5) (number-average molecular weight: 650,

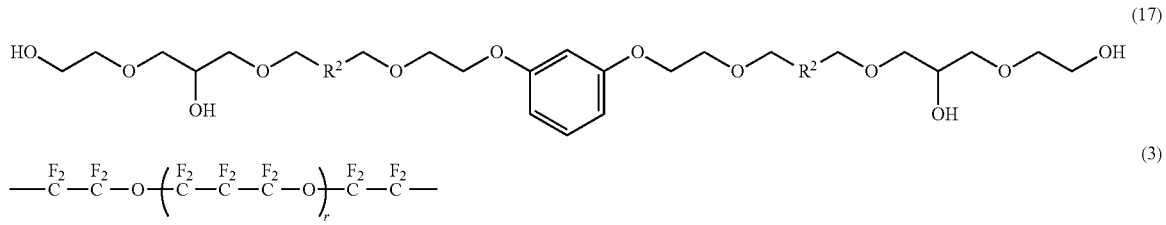

(In the formula (17), $R^2$ is represented by the following formula (3).)

(In the formula (3), r is 2.5.)

$^1$H-NMR and $^{19}$F-NMR measurements were carried out on the obtained compound (17), and the structure was identified from the following results.

(Identification Data)

$^1$H-NMR (acetone-$D_6$): δ [ppm] 3.3 to 4.2 (34H), 6.6 to 6.8 (4H)

$^{19}$F-NMR (acetone-$D_6$): δ [ppm]=−84.0 to −83.0 (20F), −86.4 (8F), −124.3 (8F), −130.0 to −129.0 (10F)

Example 10

A compound represented by the following formula (18) (4.1 g) was obtained in the same manner as in Example 1 except that fluoropolyether represented by $HOCH_2CF_2CF_2CF_2O(CF_2CF_2CF_2CF_2O)_s CF_2CF_2CF_2CH_2OH$ (in the formula, s is 1.5) (number-average molecular weight: 650, molecular weight distribution: 1.2) was used in place of the fluoropolyether represented by $HOCH_2CF_2O(CF_2CF_2O)_p(CF_2O)_qCF_2CH_2OH$ (in the formula, p is 3.0 and q is 3.0) used in Example 1, and the compound represented by the formula (14) was used in place of the compound represented by the formula (6).

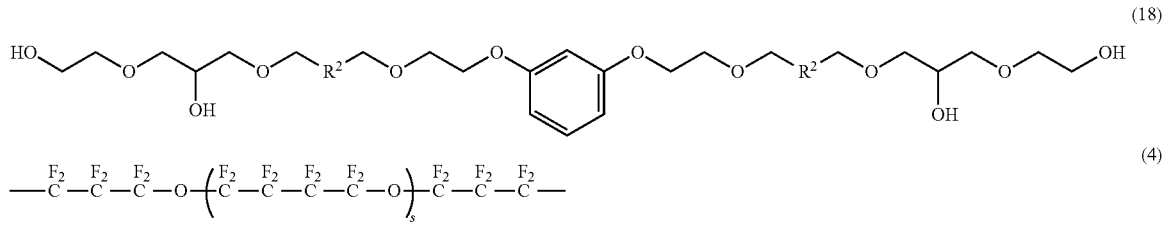

(In the formula (18), $R^2$ is represented by the following formula (4).)

(In the formula (4), s is 1.5.)

$^1$H-NMR and $^{19}$F-NMR measurements were carried out on the obtained compound (18), and the structure was identified from the following results.

(Identification Data)

$^1$H-NMR (acetone-$D_6$): δ [ppm] 3.3 to 4.2 (34H), 6.6 to 6.8 (4H)

$^{19}$F-NMR (acetone-$D_6$): δ [ppm]=−84.0 to −83.0 (20F), −122.5 (8F), −126.0 (12F), −129.0 to −128.0 (8F)

Example 11

A compound represented by the following formula (19) was synthesized in the same manner as the compound represented by the formula (6) in Example 1 except that 1,3,5-trihydroxybenzene and epichlorohydrin were used.

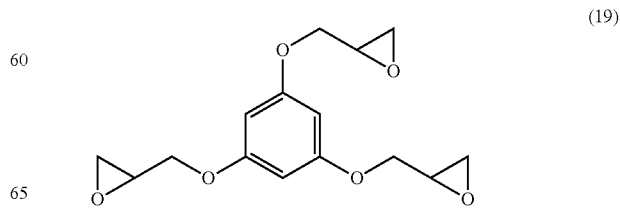

In addition, a compound represented by the following formula (20) (3.4 g) was obtained in the same manner as in Example 1 except that the compound represented by the formula (19) was used in place of the compound represented by the formula (6) used in Example 1.

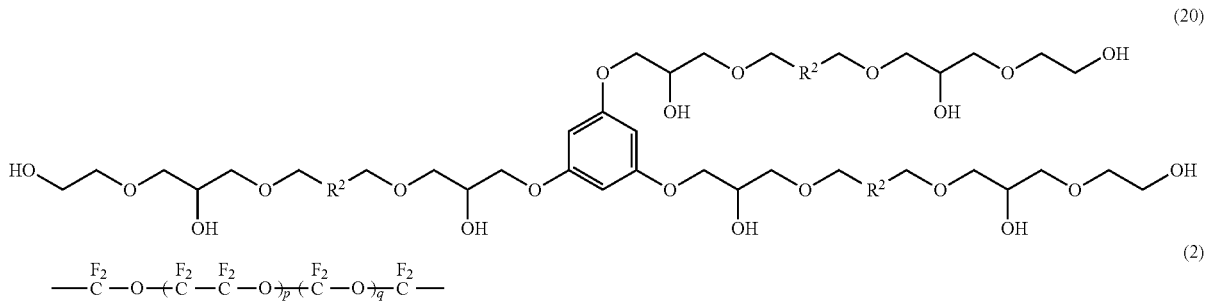

(In the formula (20), $R^2$ is represented by the following formula (2).)

(In the formula (2), p is 3.0 and q is 3.0.)

$^1$H-NMR and $^{19}$F-NMR measurements were carried out on the obtained compound (20), and the structure was identified from the following results.

(Identification Data)

$^1$H-NMR (acetone-$D_6$): δ [ppm] 3.3 to 4.2 (54H), 6.6 to 6.8 (3H)

$^{19}$F-NMR (acetone-$D_6$): δ [ppm]=−55.5 to −51.5 (18F), −78.5 (6F), −80.5 (6F), −91.0 to −88.5 (36F)

Example 12

A compound represented by the following formula (21) was synthesized in the same manner as the compound represented by the formula (14) in Example 7 except that 1,3,5-trihydroxybenzene and 1,3-dibromopropane were used.

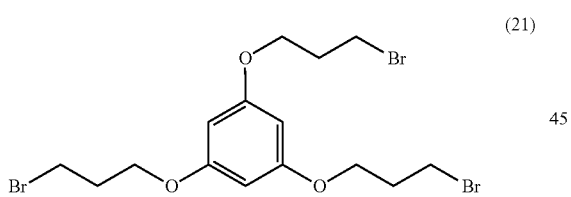

In addition, a compound represented by the following formula (22) (4.7 g) was obtained in the same manner as in Example 1 except that the compound represented by the formula (21) was used in place of the compound represented by the formula (6) used in Example 1.

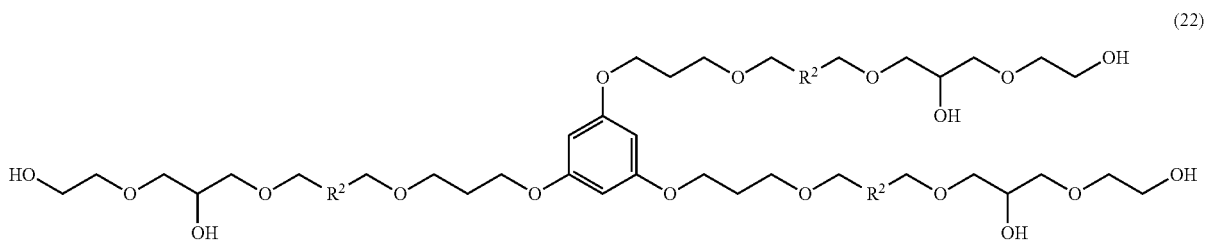

-continued

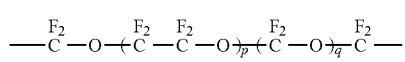
(2)

(In the formula (22), $R^2$ is represented by the following formula (2).)

(In the formula (2), p is 3.0 and q is 3.0.)

$^1$H-NMR and $^{19}$F-NMR measurements were carried out on the obtained compound (22), and the structure was identified from the following results.
(Identification Data)

$^1$H-NMR (acetone-$D_6$): δ [ppm] 3.3 to 4.2 (57H), 6.6 to 6.8 (3H)

$^{19}$F-NMR (acetone-$D_6$): δ [ppm]=−55.5 to −51.5 (18F), −78.5 (6F), −80.5 (6F), −91.0 to −88.5 (36F)

Example 13

A compound represented by the following formula (23) (4.8 g) was obtained in the same manner as in Example 1 except that fluoropolyether represented by $HOCH_2CF_2O(CF_2CF_2O)_p(CF_2O)_qCF_2CH_2OH$ (in the formula, p is 4.5 and q is 0) (number-average molecular weight: 650, molecular weight distribution: 1.2) was used in place of the fluoropolyether represented by $HOCH_2CF_2O(CF_2CF_2O)_p(CF_2O)_qCF_2CH_2OH$ (in the formula, p is 3.0 and q is 3.0) used in Example 1, and the compound represented by the formula (21) was used in place of the compound represented by the formula (6).

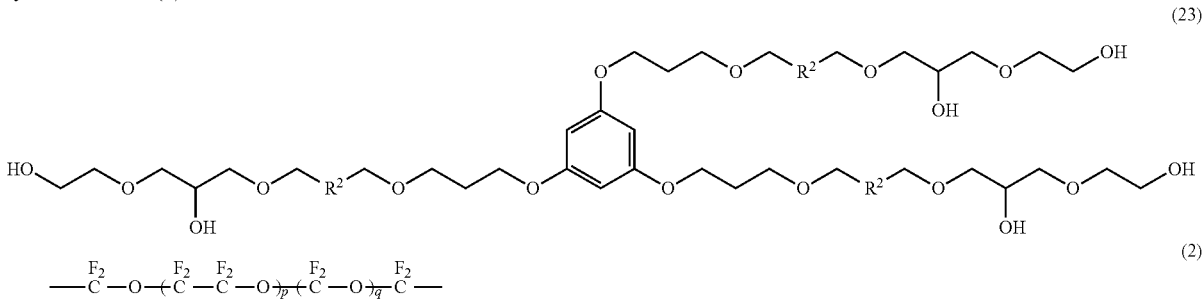

(In the formula (23), $R^2$ is represented by the following formula (2).)

(In the formula (2), p is 4.5 and q is 0.)

$^1$H-NMR and $^{19}$F-NMR measurements were carried out on the obtained compound (23), and the structure was identified from the following results.
(Identification Data)

$^1$H-NMR (acetone-$D_6$): δ [ppm] 3.3 to 4.2 (57H), 6.6 to 6.8 (3H)

$^{19}$F-NMR (acetone-$D_6$): δ [ppm]=−78.5 (6F), −81.3 (6F), −90.0 to −88.5 (54F)

Example 14

A compound represented by the following formula (24) (4.7 g) was obtained in the same manner as in Example 1 except that fluoropolyether represented by $HOCH_2CF_2CF_2O(CF_2CF_2CF_2O)_rCF_2CF_2CH_2OH$ (in the formula, r is 2.5) (number-average molecular weight: 650, molecular weight distribution: 1.2) was used in place of the fluoropolyether represented by $HOCH_2CF_2O(CF_2CF_2O)_p(CF_2O)_qCF_2CH_2OH$ (in the formula, p is 3.0 and q is 3.0) used in Example 1, and the compound represented by the formula (21) was used in place of the compound represented by the formula (6).

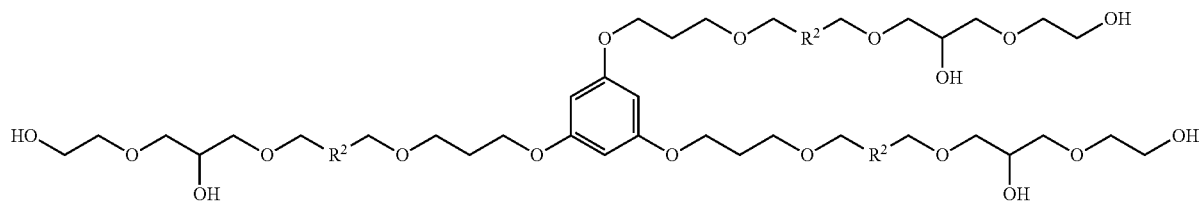

(24)

$$-\underset{F_2}{C}-\underset{F_2}{C}-O-(\underset{F_2}{C}-\underset{F_2}{C}-\underset{F_2}{C}-O)_r-\underset{F_2}{C}-\underset{F_2}{C}-$$ (3)

(In the formula (24), $R^2$ is represented by the following formula (3).)

(In the formula (3), r is 2.5.)

$^1$H-NMR and $^{19}$F-NMR measurements were carried out on the obtained compound (24), and the structure was identified from the following results.

(Identification Data)

$^1$H-NMR (acetone-$D_6$): δ [ppm] 3.3 to 4.2 (57H), 6.6 to 6.8 (3H)

$^{19}$F-NMR (acetone-$D_6$): δ [ppm]=−84.0 to −83.0 (30F), −86.4 (12F), −124.3 (12F), −130.0 to −129.0 (15F)

Example 15

A compound represented by the following formula (25) (4.2 g) was obtained in the same manner as in Example 1 except that fluoropolyether represented by $HOCH_2CF_2CF_2CF_2O(CF_2CF_2CF_2CF_2O)_s$ $CF_2CF_2CF_2CH_2OH$ (in the formula, s is 1.5) (number-average molecular weight: 650, molecular weight distribution: 1.2) was used in place of the fluoropolyether represented by $HOCH_2CF_2O(CF_2CF_2O)_p(CF_2O)_qCF_2CH_2OH$ (in the formula, p is 3.0 and q is 3.0) used in Example 1, and the compound represented by the formula (21) was used in place of the compound represented by the formula (6).

(In the formula (25), $R^2$ is represented by the following formula (4).)

(In the formula (4), s is 1.5.)

$^1$H-NMR and $^{19}$F-NMR measurements were carried out on the obtained compound (25), and the structure was identified from the following results.

(Identification Data)

$^1$H-NMR (acetone-$D_6$): δ [ppm] 3.3 to 4.2 (57H), 6.6 to 6.8 (3H)

$^{19}$F-NMR (acetone-$D_6$): δ [ppm]=−84.0 to −83.0 (30F), −122.5 (12F), −126.0 (18F), −129.0 to −128.0 (12F)

Example 16

A compound represented by the following formula (26) (4.6 g) was obtained in the same manner as in Example 1 except that the compound represented by the formula (21) was used in place of the compound represented by the formula (6) used in Example 1, and 1,3-propanediol was used in place of ethylene glycol.

(25)

$$-\underset{F_2}{C}-\underset{F_2}{C}-\underset{F_2}{C}-O-(\underset{F_2}{C}-\underset{F_2}{C}-\underset{F_2}{C}-\underset{F_2}{C}-O)_s-\underset{F_2}{C}-\underset{F_2}{C}-\underset{F_2}{C}-$$ (4)

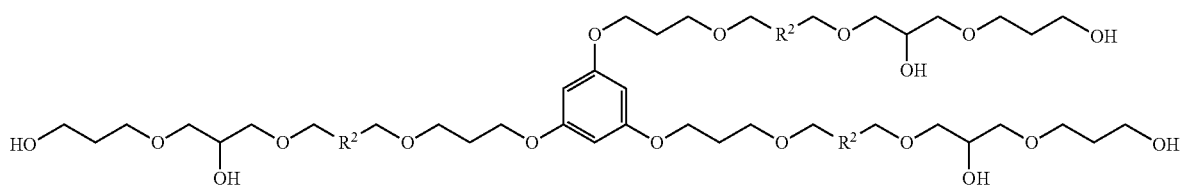

(26)

$$-\underset{F_2}{C}-O+\underset{F_2}{C}-\underset{F_2}{C}-O\underset{p}{\rightarrow}+\underset{F_2}{C}-O\underset{q}{\rightarrow}\underset{F_2}{C}-$$

(2)

(In the formula (26), $R^2$ is represented by the following formula (2).)

(In the formula (2), p is 3.0 and q is 3.0.)

$^1$H-NMR and $^{19}$F-NMR measurements were carried out on the obtained compound (26), and the structure was identified from the following results.

(Identification Data)

$^1$H-NMR (acetone-$D_6$): δ [ppm] 1.00 to 1.40 (6H), 3.3 to 4.2 (57H), 6.6 to 6.8 (3H)

$^{19}$F-NMR (acetone-$D_6$): δ [ppm]=−55.5 to −51.5 (18F), −78.5 (6F), −80.5 (6F), −91.0 to −88.5 (36F)

Example 17

A compound represented by the following formula (27) (4.6 g) was obtained in the same manner as in Example 1 except that the compound represented by the formula (21) was used in place of the compound represented by the formula (6) used in Example 1, and 1,4-butanediol was used in place of ethylene glycol.

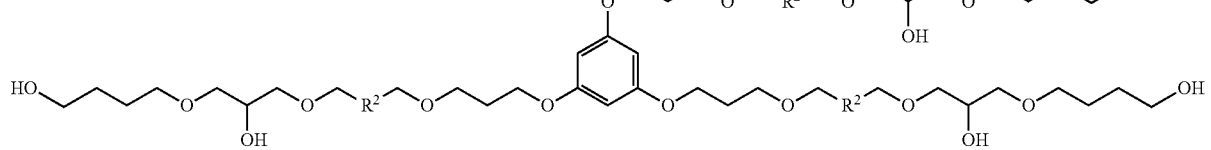

(27)

$$-\underset{F_2}{C}-O+\underset{F_2}{C}-\underset{F_2}{C}-O\underset{p}{\rightarrow}+\underset{F_2}{C}-O\underset{q}{\rightarrow}\underset{F_2}{C}-$$

(2)

(In the formula (27), $R^2$ is represented by the following formula (2).)

(In the formula (2), p is 3.0 and q is 3.0.)

$^1$H-NMR and $^{19}$F-NMR measurements were carried out on the obtained compound (27), and the structure was identified from the following results.

(Identification Data)

$^1$H-NMR (acetone-$D_6$): δ [ppm] 1.00 to 1.40 (12H), 3.3 to 4.2 (57H), 6.6 to 6.8 (3H)

$^{19}$F-NMR (acetone-$D_6$): δ [ppm]=−55.5 to −51.5 (18F), −78.5 (6F), −80.5 (6F), −91.0 to −88.5 (36F)

Comparative Example 1

A compound represented by the following formula (28) was synthesized by the method described in Patent Document 1.

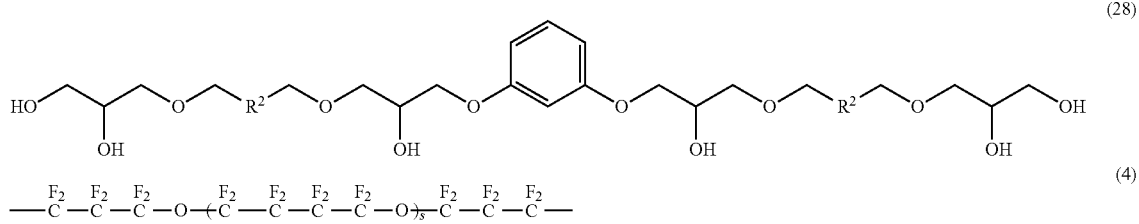

(28)

(4)

(In the formula (28), R² is represented by the following formula (4).)
(In the formula (4), s is 1.5.)

Comparative Example 2

A compound represented by the following formula (29) was synthesized by the method described in Patent Document 1.

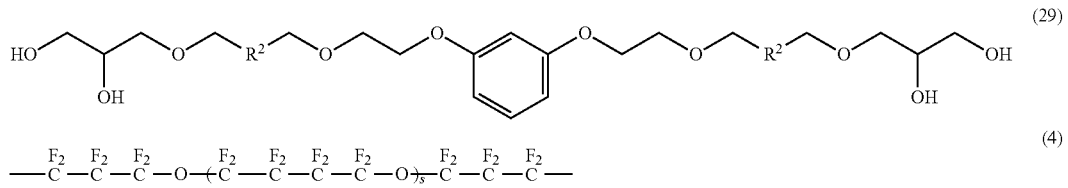

(29)

(4)

(In the formula (29), R² is represented by the following formula (4).)
(In the formula (4), s is 1.5.)

Comparative Example 3

A compound represented by the following formula (30) was synthesized by the method described in Patent Document 2.

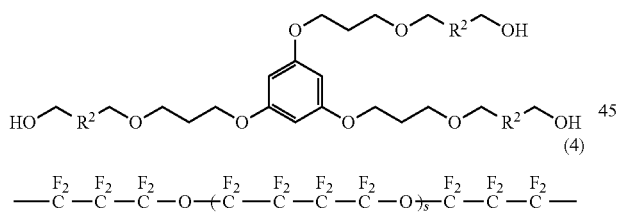

(30)

(4)

(In the formula (30), R² is represented by the following formula (4).)
(In the formula (4), s is 1.5.)

Comparative Example 4

A compound represented by the following formula (31) was synthesized by the method described in Patent Document 3.

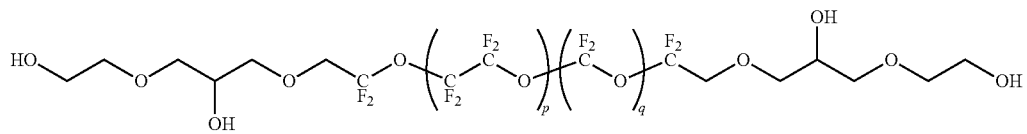

(31)

(In the formula (31), p is 9.0 and q is 9.0.)

The number of n (the number of benzene substituents) in the formula (1), the number of m in $R^3$, and the structures of $R^1$ and $R^2$ in the compounds of Examples 1 to 17 obtained as described above are shown in Table 1.

TABLE 1

| | Compound | Number of benzene substituents | R1 | R2 | R3 | |
|---|---|---|---|---|---|---|
| Example 1 | (5) | 2 | —CH$_2$CH(OH)CH$_2$— | Formula (2) | p = 3.0, q = 3.0 | m = 2 |
| Example 2 | (9) | 2 | —CH$_2$CH(OH)CH$_2$— | Formula (2) | p = 4.5, q = 0 | m = 2 |
| Example 3 | (10) | 2 | —CH$_2$CH(OH)CH$_2$— | Formula (3) | r = 2.5 | m = 2 |
| Example 4 | (11) | 2 | —CH$_2$CH(OH)CH$_2$— | Formula (4) | s = 1.5 | m = 2 |
| Example 5 | (12) | 2 | —CH$_2$CH(OH)CH$_2$— | Formula (2) | p = 3.0, q = 3.0 | m = 3 |
| Example 6 | (13) | 2 | —CH$_2$CH(OH)CH$_2$— | Formula (2) | p = 3.0, q = 3.0 | m = 4 |
| Example 7 | (15) | 2 | —CH$_2$CH$_2$— | Formula (2) | p = 3.0, q = 3.0 | m = 2 |
| Example 8 | (16) | 2 | —CH$_2$CH$_2$— | Formula (2) | p = 4.5, q = 0 | m = 2 |
| Example 9 | (17) | 2 | —CH$_2$CH$_2$— | Formula (3) | r = 2.5 | m = 2 |
| Example 10 | (18) | 2 | —CH$_2$CH$_2$— | Formula (4) | s = 1.5 | m = 2 |
| Example 11 | (20) | 3 | —CH$_2$CH(OH)CH$_2$— | Formula (2) | p = 3.0, q = 3.0 | m = 2 |
| Example 12 | (22) | 3 | —CH$_2$CH$_2$CH$_2$— | Formula (2) | p = 3.0, q = 3.0 | m = 2 |
| Example 13 | (23) | 3 | —CH$_2$CH$_2$CH$_2$— | Formula (2) | p = 4.5, q = 0 | m = 2 |
| Example 14 | (24) | 3 | —CH$_2$CH$_2$CH$_2$— | Formula (3) | r = 2.5 | m = 2 |
| Example 15 | (25) | 3 | —CH$_2$CH$_2$CH$_2$— | Formula (4) | s = 1.5 | m = 2 |
| Example 16 | (26) | 3 | —CH$_2$CH$_2$CH$_2$— | Formula (2) | p = 3.0, q = 3.0 | m = 3 |
| Example 17 | (27) | 3 | —CH$_2$CH$_2$CH$_2$— | Formula (2) | p = 3.0, q = 3.0 | m = 4 |

The number-average molecular weights of the compounds of Examples 1 to 17 and Comparative Examples 1 to 4 obtained as described above were obtained by the above-described $^1$H-NMR and $^{19}$F-NMR measurements. The results are shown in Table 2.

TABLE 2

| | Compound | Number-average molecular weight | Film thickness (Å) | Bond rate % | Bond rate Evaluation | Pickup suppression test | Wear resistance test | Comprehensive evaluation |
|---|---|---|---|---|---|---|---|---|
| Example 1 | (5) | 1907 | 9.5 | 73% | A | AA | AA | AA |
| Example 2 | (9) | 1859 | 9.5 | 71% | A | AA | AA | AA |
| Example 3 | (10) | 1905 | 9.5 | 70% | A | AA | AA | AA |
| Example 4 | (11) | 1893 | 9.5 | 73% | A | AA | AA | AA |
| Example 5 | (12) | 1935 | 9.5 | 71% | A | AA | AA | AA |
| Example 6 | (13) | 1963 | 9.5 | 72% | A | AA | AA | AA |
| Example 7 | (15) | 1847 | 9.5 | 67% | A | AA | AA | AA |
| Example 8 | (16) | 1799 | 9.5 | 69% | A | AA | AA | AA |
| Example 9 | (17) | 1845 | 9.5 | 69% | A | AA | AA | AA |
| Example 10 | (18) | 1833 | 9.5 | 68% | A | AA | AA | AA |
| Example 11 | (20) | 2821 | 10.0 | 74% | A | AA | AA | AA |
| Example 12 | (22) | 2773 | 10.0 | 70% | A | AA | AA | AA |
| Example 13 | (23) | 2701 | 9.5 | 72% | A | AA | AA | AA |
| Example 14 | (24) | 2770 | 9.5 | 73% | A | AA | AA | AA |
| Example 15 | (25) | 2752 | 10.0 | 72% | A | AA | AA | AA |
| Example 16 | (26) | 2815 | 10.0 | 70% | A | AA | AA | AA |
| Example 17 | (27) | 2899 | 10.0 | 71% | A | AA | AA | AA |
| Comparative Example 1 | (28) | 1805 | 9.5 | 62% | B | C | A | B |
| Comparative Example 2 | (29) | 1744 | 9.5 | 58% | B | C | B | B |
| Comparative Example 3 | (30) | 2620 | 10.0 | 35% | C | C | A | C |
| Comparative Example 4 | (31) | 2052 | 9.5 | 40% | C | C | A | C |

In Table 2, "AA" means an excellent result, "A" means a favorable result, "B" means a permissible result, and "C" means an impermissible result.

Next, solutions for forming a lubricating layer were prepared using the compounds obtained in Examples 1 to 17 and Comparative Examples 1 to 4 by a method described below. In addition, lubricating layers for magnetic recording media were formed using the obtained solutions for forming a lubricating layer by a method described below, and magnetic recording media of Examples 1 to 17 and Comparative Examples 1 to 4 were obtained.

"Solutions for Forming Lubricating Layer"

The compounds obtained in Examples 1 to 17 and Comparative Examples 1 to 4 were dissolved in VERTREL (registered trademark) XF (trade name, manufactured by Dupont-Mitsui Fluorochemicals Co., Ltd.), which is a fluorine-based solvent, diluted with VERTREL XF such that the film thicknesses reached 9 Å to 10 Å when applied onto protective layers and used as solutions for forming a lubricating layer.

"Magnetic Recording Media"

Magnetic recording media each having an adhesive layer, a soft magnetic layer, a first underlayer, a second underlayer, a magnetic layer and a protective layer sequentially provided on a substrate having a diameter of 65 mm were prepared. As the protective layer, a carbon layer was used.

The solutions for forming a lubricating layer of Examples 1 to 17 and Comparative Examples 1 to 4 were applied onto the protective layers of the magnetic recording media, in which the individual layers up to the protective layer had been formed, by the dipping method. The dipping method was carried out under conditions of an immersion speed of 10 mm/sec, an immersion time of 30 seconds and a lifting speed of 1.2 mm/sec.

After that, the magnetic recording media to which the solutions for forming a lubricating layer had been applied were put into a thermostatic chamber (120° C.) and heated for 10 minutes to remove the solvents in the solutions for forming a lubricating layer, thereby forming lubricating layers on the protective layers and obtaining magnetic recording media.

The film thicknesses of the lubricating layers in the magnetic recording media of Examples 1 to 17 and Comparative Examples 1 to 4 obtained as described above were measured using FT-IR (trade name: Nicolet iS50, manufactured by Thermo Fisher Scientific). The results are shown in Table 2.

In addition, on the magnetic recording media of Examples 1 to 17 and Comparative Examples 1 to 4, the measurement of the adhesion (bond rate) between the lubricating layer and the protective layer, pickup suppression tests and wear resistance tests, which will be described below, were carried out. The results are shown in Table 2.

(Measurement of Adhesion (Bond Rate) Between Lubricating Layer and Protective Layer)

The magnetic recording medium in which the lubricating layer was formed was washed by a method in which the magnetic recording medium was immersed in VERTREL XF, which was a solvent, for 10 minutes and lifted. The speed of immersing the magnetic recording medium into the solvent was set to 10 mm/sec, and the lifting speed was set to 1.2 mm/sec.

After that, the film thickness of the lubricating layer was measured by the same method as for the measurement of the film thickness of the lubricating layer before the washing.

In addition, the film thickness of the lubricating layer before the washing was defined as A, the film thickness of the lubricating layer after the washing (after the immersion in the solvent) was defined as B, and the bonding rate (bond rate) of the lubricant was calculated from the ratio between A and B ((B/A)×100(%)). The adhesion between the lubricating layer and the protective layer was evaluated by references described below using the calculated bond rate.

"Evaluation of Adhesion (Bond Rate)"

A (Favorable): The bond rate is 65% or more.

B (Permissible): The bond rate is 50% or more and less than 65%.

C (Impermissible): The bond rate is less than 50%.

(Pickup Suppression Test)

The magnetic recording medium and a magnetic head were mounted in a spin stand, and the magnetic head was floated at a fixed point for 10 minutes while rotating the magnetic recording medium at normal temperature under reduced pressure (approximately 250 torr). After that, the surface of the magnetic head that faced the magnetic recording medium (the surface of the lubricating layer) was analyzed using an analyzer for electron spectroscopy for chemical analysis (ESCA). In addition, the amount of the lubricant attached to the magnetic head was evaluated by references shown in Table 3 based on the intensity (signal intensity (a.u.)) of a fluorine-derived peak measured by ESCA.

TABLE 3

| Evaluation | Signal intensity | ESCA signal intensity |
|---|---|---|
| AA | 500 or less | No lubricant is attached to the head, and the signal intensity does not change. |
| A | More than 500 and 1000 or less | The lubricant is slightly attached to the head, and the signal intensity is small. |
| C | More than 1000 | A large amount of the lubricant is attached to the head, and the signal intensity is large. |

In Table 3, "AA" means an excellent result, "A" means a favorable result, and "C" means an impermissible result.

(Wear Resistance Test)

An alumina sphere having a diameter of 2 mm, which was a contact, was slid on the lubricating layers of the magnetic recording media at a load of 40 gf and a sliding speed of 0.25 m/sec using a pin-on disc-type friction wear tester, and the friction coefficients of the surfaces of the lubricating layers were measured. In addition, the sliding times until the friction coefficients of the surfaces of the lubricating layers sharply increased were measured. The sliding time until the friction coefficient sharply increased was measured four times for the lubricating layer of each magnetic recording medium, and the average value (time) was used as an index of the wear resistance of a lubricant coating.

On the magnetic recording media of Examples 1 to 17 and Comparative Examples 1 to 4, the wear resistances were evaluated based on the sliding times until the friction coefficient sharply increased as described below.

"Evaluation of Wear Resistance (Sliding Time)"

AA (Excellent): 650 seconds or longer

A (Favorable): 550 seconds or longer and shorter than 650 seconds

B (Permissible): 450 seconds or longer and shorter than 550 seconds

C (Impermissible): Shorter than 450 seconds

The time until the friction coefficient sharply increases can be used as an index of the wear resistance of the lubricating layers for the reason described below. The reason is that the use of the magnetic recording medium leads to wear of the lubricating layer in the magnetic recording medium, and, once the lubricating layer disappears due to the wear, the contact and the protective layer come into direct contact with each other, and the friction coefficient sharply increases. The time until the friction coefficient sharply increases is also considered to correlate with friction tests.

As shown in Table 2, in Examples 1 to 17, the evaluation result of the adhesion (bond rates) between the lubricating layer and the protective layer and the results of the pickup suppression tests and the wear resistance tests were all favorable. In contrast, in Comparative Example 1 and Comparative Example 2 in which a compound having, not —OCH$_2$CH(OH)CH$_2$O(CH$_2$)$_m$OH (m in the formula is an integer of 2 to 4), but —OCH$_2$CH(OH)CH$_2$OH as the terminal group was used, the pickup suppression tests were evaluated as impermissible (C).

In addition, in Comparative Example 3 in which a compound having —OH as the terminal group was used, the bond rate and the pickup suppression test were evaluated as impermissible (C).

In addition, in Comparative Example 4 in which a compound having a perfluoropolyether chain disposed in the center of the molecule was used, the bond rate and the pickup suppression test were evaluated as impermissible (C).

In Comparative Examples 1 to 4, all results of the bond rates, the pickup suppression tests and the wear resistance tests thereof were poor compared with those of Examples 1 to 17.

From the above-described results, it was found that, when a lubricating layer containing the compound of Examples 1 to 17 is formed on a protective layer in a magnetic recording medium, a lubricating layer in which the adhesion to a protective layer is excellent, pickup is unlikely to occur and wear resistance is excellent can be obtained in spite of a thin thickness of 9 Å to 10 Å.

INDUSTRIAL APPLICABILITY

The present invention is capable of providing a fluorine-containing ether compound that enables the formation of a lubricating layer in which wear resistance is excellent and pickup is suppressed in spite of a thin thickness, and can be preferably used as a material for lubricants for magnetic recording media. The use of a lubricant for a magnetic recording medium containing the fluorine-containing ether compound of the present invention enables the formation of a lubricating layer in which wear resistance is excellent and pickup is suppressed in spite of a thin thickness.

REFERENCE SIGNS LIST

10 Magnetic recording medium
11 Substrate
12 Adhesive layer
13 Soft magnetic layer
14 First underlayer
15 Second underlayer
16 Magnetic layer
17 Protective layer
18 Lubricating layer

The invention claimed is:

1. A fluorine-containing ether compound represented by the following formula (1),

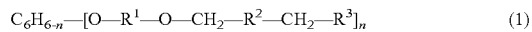

(in the formula (1), n is an integer of 2 or 3, $R^1$ is any one of —$CH_2CH_2$—, —$CH_2CH_2CH_2$— and —$CH_2CH(OH)CH_2$—, $R^2$ is a perfluoropolyether chain, $R^3$ is —$OCH_2CH(OH)CH_2O(CH_2)_mOH$ (m in the formula is an integer of 2 to 4)).

2. The fluorine-containing ether compound according to claim 1, wherein $R^2$ in the formula (1) is represented by any one of the following formulae (2) to (4),

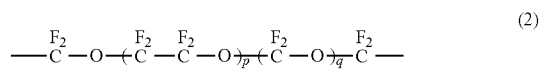

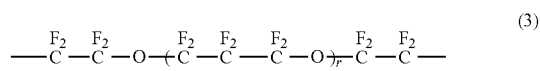

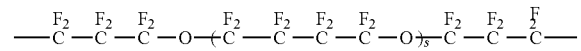

(in the formula (2), p represents 1 to 30, and q represents 0 to 30),
(in the formula (3), r represents 1 to 30), and
(in the formula (4), s represents 1 to 20).

3. The fluorine-containing ether compound according to claim 2, wherein the compound is any one of compounds represented by the following formulae (A) to (N),

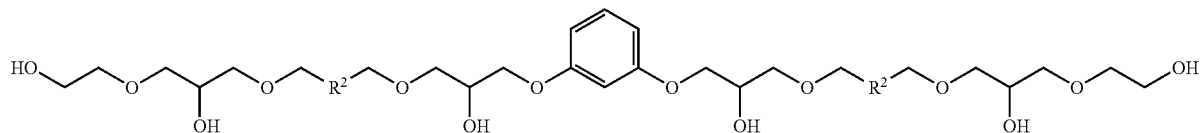

(A)

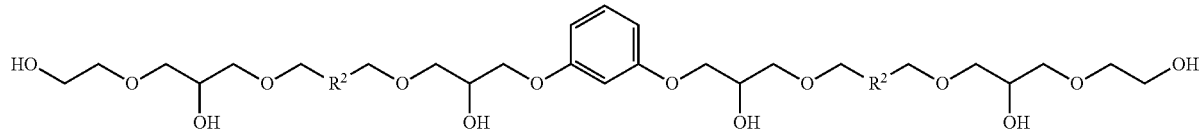

(B)

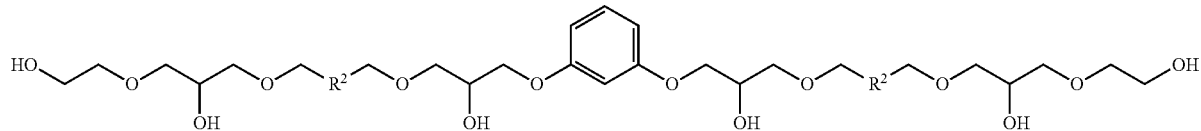

(C)

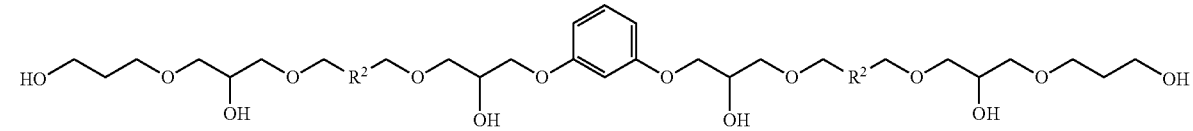

(D)

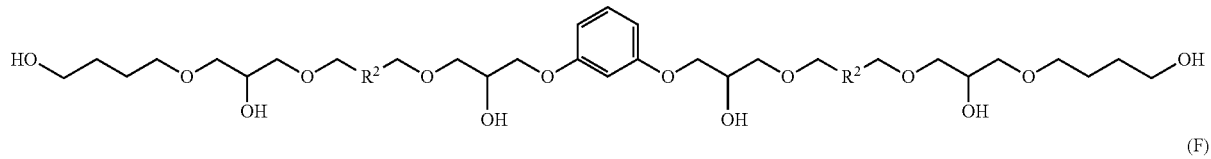

(E)

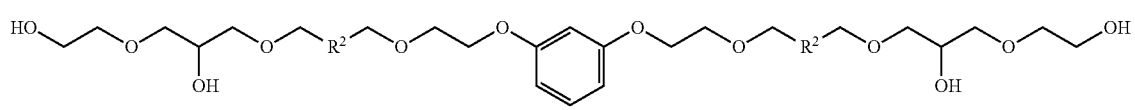

(F)

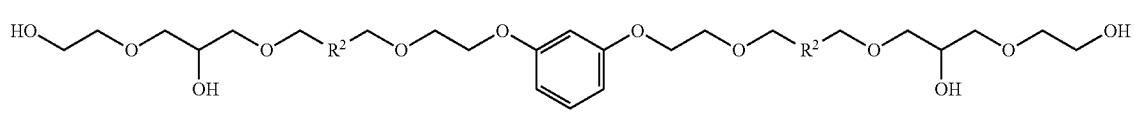

(G)

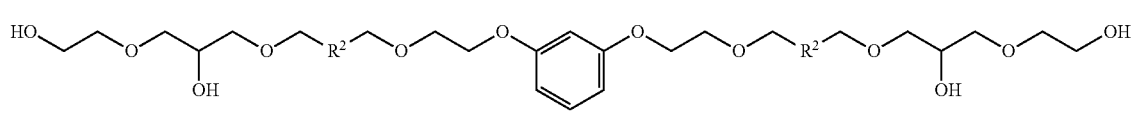

(H)

(in the formula (A), R² is represented by the formula (2)),
(in the formula (B), R² is represented by the formula (3)),
(in the formula (C), R² is represented by the formula (4)),
(in the formula (D), R² is represented by the formula (2)),
(in the formula (E), R² is represented by the formula (2)), (in the formula (F), R² is represented by the formula (2)),
(in the formula (G), R² is represented by the formula (3)),
and
(in the formula (H), R² is represented by the formula (4)),

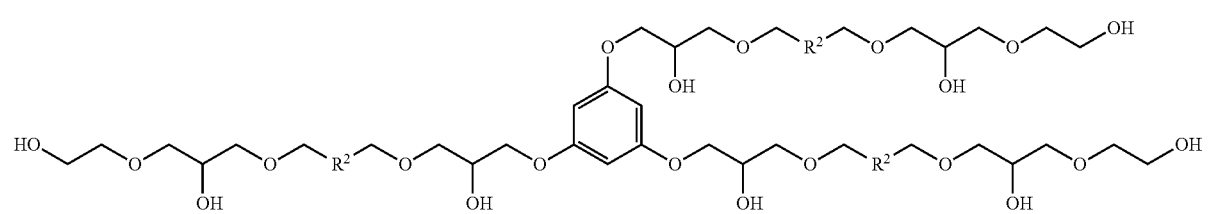

(I)

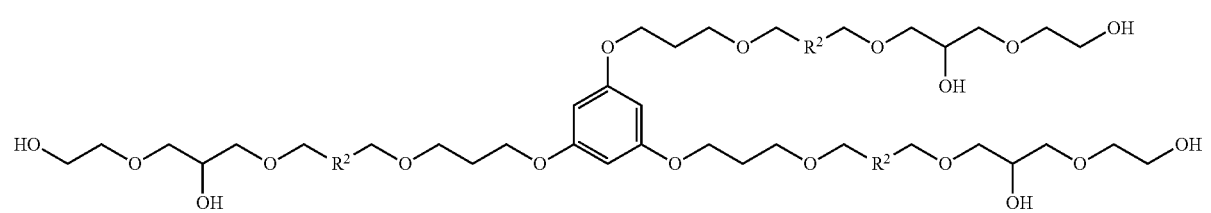

(J)

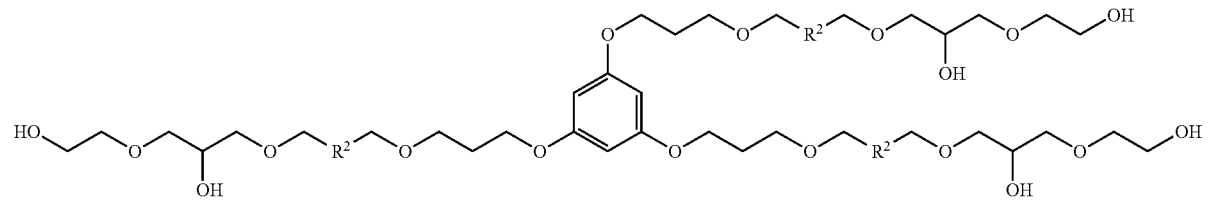

(K)

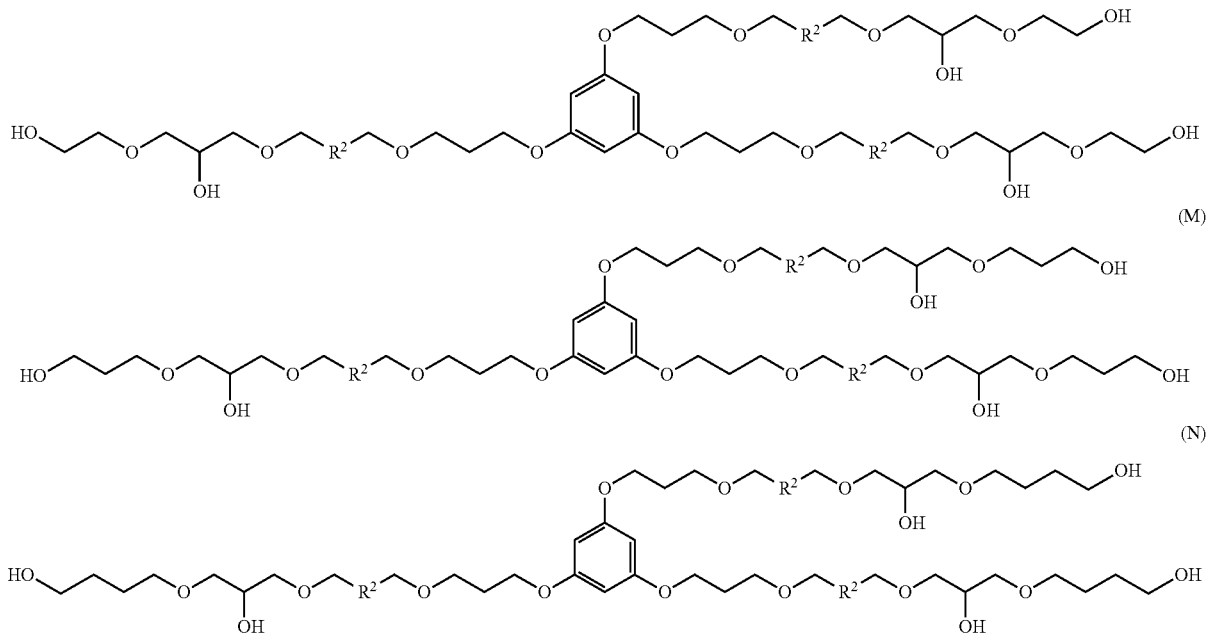

(in the formula (I), R² is represented by the formula (2)),
(in the formula (J), R² is represented by the formula (2)),
(in the formula (K), R² is represented by the formula (3)),
(in the formula (L), R² is represented by the formula (4)),
(in the formula (M), R² is represented by the formula (2)), and
(in the formula (N), R² is represented by the formula (2)).

4. The fluorine-containing ether compound according to claim 1,
wherein a number-average molecular weight thereof is within a range of 500 to 10000.

5. A lubricant for a magnetic recording medium, comprising: the flourine-containing ether compound according to claim 1.

6. A magnetic recording medium, comprising at least:
a magnetic layer;
a protective layer; and
a lubricating layer sequentially provided on a substrate,
wherein the lubricating layer contains the fluorine-containing ether compound according to claim 1.

7. The magnetic recording medium according to claim 6,
wherein the lubricating layer has an average film thickness of 0.5 nm to 3 nm.

* * * * *